US007255867B2

(12) United States Patent
Lowell et al.

(10) Patent No.: US 7,255,867 B2
(45) Date of Patent: Aug. 14, 2007

(54) VACCINE

(75) Inventors: George H Lowell, Hampstead (CA); George L White, Beaconsfield (CA); Michael R Batzloff, Coopers Plains (AU); David S Burt, Dollard Des Ormeaux (CA); Tomas B Leanderson, Malmo (SE); Michael F Good, The Gap (AU)

(73) Assignees: ID Biomedical Corporation of Quebec, Laval, Quebec (CA); The Council of the Queensland Institute of Medical Research, Herston Queensland (AU)

( * ) Notice: Subject to any disclaimer, the term of this patent is extended or adjusted under 35 U.S.C. 154(b) by 47 days.

(21) Appl. No.: 10/706,275

(22) Filed: Nov. 13, 2003

(65) Prior Publication Data

US 2005/0002956 A1   Jan. 6, 2005

Related U.S. Application Data

(60) Provisional application No. 60/426,409, filed on Nov. 15, 2002.

(30) Foreign Application Priority Data

Nov. 15, 2002  (AU) .............................. 2002302132

(51) Int. Cl.
  *A61K 39/09* (2006.01)
  *A61K 39/00* (2006.01)
  *A61K 39/385* (2006.01)
  *A61K 45/00* (2006.01)
  *A61K 9/127* (2006.01)
  *A61K 38/00* (2006.01)
  *A01N 37/18* (2006.01)

(52) U.S. Cl. .............................. 424/244.1; 424/184.1; 424/237.1; 424/234.1; 424/236.1; 424/185.1; 424/193.1; 424/450; 424/454; 424/283.1; 424/197.11; 514/2; 514/8; 514/12

(58) Field of Classification Search ............. 424/184.1, 424/244.1, 237.1, 185.1, 193.1, 450, 234.1, 424/283.1, 197.11, 454, 236.1; 514/12, 8, 514/2

See application file for complete search history.

(56) References Cited

U.S. PATENT DOCUMENTS

| 4,454,121 | A |   | 6/1984  | Beachey .................... 424/177 |
| 4,521,334 | A |   | 6/1985  | Beachey .................. 260/112.5 |
| 4,597,967 | A |   | 7/1986  | Beachey ..................... 424/88 |
| 4,695,562 | A |   | 9/1987  | Beachey et al. ............... 514/13 |
| 4,705,684 | A |   | 11/1987 | Beachey ...................... 424/88 |
| 4,707,543 | A | * | 11/1987 | Zollinger et al. ........... 530/402 |
| 4,728,639 | A |   | 3/1988  | Beachey ...................... 514/12 |
| 4,919,930 | A |   | 4/1990  | Beachey et al. ............... 424/88 |
| 5,124,153 | A |   | 6/1992  | Beachey et al. ............ 424/93 P |
| 5,162,226 | A |   | 11/1992 | Beachey et al. .......... 435/252.3 |
| 5,716,637 | A | * | 2/1998  | Anselem et al. .............. 424/450 |
| 5,726,292 | A | * | 3/1998  | Lowell ........................ 530/403 |
| 5,961,970 | A | * | 10/1999 | Lowell et al. .............. 424/93.1 |
| 5,965,390 | A | * | 10/1999 | Bjorck et al. .............. 435/69.1 |
| 5,985,284 | A |   | 11/1999 | Lowell ..................... 424/234.1 |
| 6,063,386 | A | * | 5/2000  | Dale et al. ............... 424/244.1 |
| 6,174,528 | B1 | * | 1/2001  | Cooper et al. ........... 424/184.1 |
| 6,419,932 | B1 | * | 7/2002  | Dale ........................ 424/244.1 |
| 6,476,201 | B1 | * | 11/2002 | Lowell et al. .............. 530/414 |
| 6,716,433 | B1 |   | 4/2004  | Dale ........................ 424/244.1 |
| 6,737,521 | B1 | * | 5/2004  | Fischetti et al. ........... 536/23.4 |
| 6,743,900 | B2 |   | 6/2004  | Burt et al. .................. 530/414 |
| 6,803,042 | B2 | * | 10/2004 | Lowell ..................... 424/250.1 |
| 6,822,075 | B2 | * | 11/2004 | Bjorck et al. ............... 530/350 |
| 7,060,277 | B2 | * | 6/2006  | Kaempfer et al. ........ 424/184.1 |
| 7,189,398 | B2 | * | 3/2007  | Kaempfer et al. ........ 424/184.1 |
| 2002/0086023 | A1 |   | 7/2002  | Dale ........................ 424/178.1 |
| 2002/0176863 | A1 |   | 11/2002 | Dale ........................ 424/184.1 |
| 2003/0143245 | A1 |   | 7/2003  | Reddish et al. ........... 424/190.1 |
| 2003/0157122 | A1 |   | 8/2003  | Dale ........................ 424/190.1 |
| 2005/0002956 | A1 | * | 1/2005  | Lowell et al. ............ 424/190.1 |
| 2005/0042230 | A1 |   | 2/2005  | Anderson et al. ......... 424/186.1 |
| 2005/0063988 | A1 |   | 3/2005  | Dale ........................ 424/190.1 |
| 2005/0152919 | A1 |   | 7/2005  | Ward et al. ............... 424/212.1 |
| 2005/0202037 | A1 |   | 9/2005  | Dale ........................ 424/190.1 |
| 2006/0222650 | A1 | * | 10/2006 | Kaempfer et al. ........ 424/164.1 |

FOREIGN PATENT DOCUMENTS

EP    0 305 279 A1   3/1989

(Continued)

OTHER PUBLICATIONS

Lowell et al, Technological Advances in Vaccine Development, 1988, pp. 423-432.*

(Continued)

*Primary Examiner*—N. M. Minnifield
(74) *Attorney, Agent, or Firm*—Seed IP Law Group PLLC

(57) ABSTRACT

Effective stimulation of immune responses is achieved through the use of a group A streptococcal antigen combined with proteosome adjuvant. The compositions are provided in particular for intranasal administration. The vaccine compositions are provided for use in inducing an immune response in an individual for the treatment or prophylaxis of group A streptococcal infection in an individual, preferably via prevention or reduction of colonisation of the throat following intranasal administration.

13 Claims, 22 Drawing Sheets

FOREIGN PATENT DOCUMENTS

| | | | |
|---|---|---|---|
| WO | WO 90/15872 A1 * | 12/1990 | |
| WO | WO 93/21220 A1 * | 10/1993 | |
| WO | WO 94/06421 A1 * | 3/1994 | |
| WO | WO 94/06465 A1 * | 3/1994 | |
| WO | WO 96/11944 A1 * | 4/1996 | |
| WO | WO 97/10844 A1 * | 3/1997 | |
| WO | WO 98/01558 A2 | 1/1998 | |
| WO | WO 98/34968 A1 * | 8/1998 | |
| WO | WO 99/13084 A1 | 3/1999 | |
| WO | WO 99/52939 A1 * | 10/1999 | |
| WO | WO 00/37648 A1 | 6/2000 | |
| WO | WO 00/40729 A1 | 7/2000 | |
| WO | WO 01/60402 A2 | 8/2001 | |
| WO | WO 02/057315 A2 | 7/2002 | |
| WO | WO 02/072012 A2 * | 9/2002 | |
| WO | WO 03/065973 A2 | 8/2003 | |
| WO | WO 2004/098636 A2 | 11/2004 | |
| WO | WO 2005/007189 A1 | 1/2005 | |
| WO | WO 2005/027964 A1 | 3/2005 | |
| WO | WO 2005/042017 A1 | 5/2005 | |

OTHER PUBLICATIONS

Olive et al, Vaccine, 2002, 20:2816-2825.*
Hayman et al, Immunology and Cell Biology, 2002, 80:178-187.*
Batzloff et al, Indian J. Med. Res., May 2004, 119/Suppl:104-107.*
Toth et al, PEPTIDES 2002, pp. 634-635.*
Musser et a al, Infection and Immunity, Mar. 1995, 63/3:994-1003.*
Berge et al, JBC, 1993, 268/34:25417-25424.*
Podbielski et al, Med. Microbiol. Immunol., 1992, 181:209-213.*
Collins et al, Infection and Immunity, 1992, 60/9:3689-3696.*
Smirnov et al, Gene, 1992, 120:27-32.*
Hall et al, Infection and Immunity, May 2004, 72/5"2507-2512.*
Whatmore et al, Molecular Microbiology, 1994, 14/4:619-631.*
Lesinki et al, Abstracts of Gener al Meeting American Society for Microbiology, 2001, 101:341 abstract only.*
Bessen et al, Infection and Immunity, 1988, 56/10:2666-2672.*
Brandt et al, International Immunology, 1999, 11/4:569-576.*
Brandt et al, Nature Medicine, 2000, 6/4:455-459.*
Brandt et al, Immunology, 1996, 89:331-337.*
Hayman et al, International Immunology, 1997, 9/11:1723-1733.*
Relf et al, Advances in Exptal. Med. and Biol., 1997, 418(Streptococci and the Host):859-861.*
Fox et al J. Clinical Investigation, 1973, 52:1885-1892.*
Bessen et al, J. Immunology, 1990, 145/4:1251-1256.*
Horvath et al, J. Med. Chem., 2004, 47:4100-4104.*
Olive et al, Infection and Immuinty, 2002, 70/5:2734-2738.*
Brandt et al, Infection and Immunity, 2000, 68/12:6587-6594.*
Dunn et al, Vaccine, 2002, 20:2635-2640.*
Lesinski et al, Vaccine, 2001, 19:1717-1726.*
Dale, Vaccine, 1999, 17:193-200.*
Olive et al, Vaccine, 2005, 23:2298-2303.*
Srivastava et al, Hybridoma, 2000, 19/1:23-31.*
Relf et al, Peptide Research, 1996, 9/1:12-20.*
Lowell et al, Infection and Immunity, 1996, 64/5:1706-1713.*
Kaminski et al, 94th ASM General Meeting, 1994, 94/0:155 Abstract #E-70 Abstract only.*
Lowell et al, Trans. Royal Soc. Trop. Med. and Hyg., 1989, 83/Suppl:101-102.*
Bhattacharjee et al, J. Infectious Diseases, 1996, 173:1157-1163.*
Dasleg et al, Vaccines, 1996, pp. 177-182.*
Fries et al, Infection and Immunity, 2001, 69/7:4545-4553.*
Plante et al, International Congress Series, 2001, 1219:979-984.*
Ruegg et al, J. Immunological Methods, 1990, 135:101-109.*
Mallett et al, Infection and Immunity, 1995, 63/6:2382-2386.*
Lowell et al, Infection and Immunity, 1996, 64/11:4686-4693.*
Lowell et al, Science, 1988, 240:800-802.*
Levi et al, Vaccine, 1995, 13/14:1353-1359.*
Lynch et al, Biophys. J. 1984, 45:104-107.*
Lowell, In: New Generation Vaccines, ed. Levine et al, 1997 Marcel Dekker, Inc., pp. 193-206.*
Lowell et al, J, Expt. Medicine, 1988, 167:658-663.*
Cunningham, Clinical Microbiology Reviews, 2000, 13/3:470-511.*
Dale, Infect. Dis. Clin. North Am., 1999, 13/1:227-243 abstract only.*
Dale et al, Infection and Immunity, 2002, 70/4:2166-2170.*
Pruksakorn et al, J. Immunology, 1992, 149/8:2729-2735.*
Hu et al, Infection and Immunity, 2002, 70/4:2171-2177.*
Dale et al, J. Clin. Invest., 1999, 103/9:1261-1268.*
Bronze, M. S. et al., "Epitopes of group A streptococcal M protein that evoke cross-protective local immune responses," *The Journal of Immunology*, 148(3):888-893, Feb. 1, 1992.
Cartwright, K., "Group A streptococcal infections in humans," *Journal of Applied Microbiology Symposium*, 83(Suppl.):52S-61S, 1997.
Guzman, C. A. et al., "Protective immune response against *Streptococcus pyogenes* in mice after intranasal vaccination with Fibronectin-Binding protein Sfbl," *The Journal of Infectious Diseases*, 179(4):901-906, Apr. 1999.
Janulczyk, R. et al., "Identification and characterization of a *Streptococcus pyogenes* ABC transporter with multiple specificity for metal cations," *Molecular Microbiology*, 34(3):596-606, 1999.
Ji, Y. et al., "Intranasal immunization with C5a peptidase prevents nasopharyngeal colonization of mice by group A *Streptococcus*," *Infection and Immunity*, 65(6):2080-2087, Jun. 1997.
Johnsson, E. et al, "Role of hypervariable region in streptococcal M proteins: Binding of a human complement inhibitor," *The Journal of Immunology*, 161(9):4894-4901, 1998.
Kehoe, M. A. et al., "Horizontal gene transfer among group A streptococci: implications for pathogenesis and epidemiology," *Trends in Microbiology*, 4(11):436-443, Nov. 1996.
Pruksakorn, S. et al., "Identification of T-cell autoepitopes that cross-react with the C- terminal segment of the M protein of group A streptococci," *International Immunology*, 6(8):1235-1244, 1994.
Pruksakorn, S. et al., "Towards a vaccine for rheumatic fever: identification of a conserved target epitope on M protein of group A streptococci," *The Lancet*, 344:639-642, Sep. 3, 1994.
Robinson, J. H. and Kehoe, M. A., "Group A streptococcal M proteins: virulence factors and protective antigens," *Immunology Today*, 13(9):362-367, 1992.

* cited by examiner

```
p145            LRRDLDASREAKKQVEKALE
J1         QLEDKVKQLRRDLDASREAKEELQDKVK
J2          LEDKVKQARRDLDASREAKKELQDKVKQ
J3           EDKVKQAERDLDASREAKKQLQDKVKQL
J4            DKVKQAEDDLDASREAKKQVQDKVKQLE
J5             KVKQAEDKLDASREAKKQVEDKVKQLED
J6              VKQAEDKVDASREAKKQVEKKVKQLEDK
J7               KQAEDKVKASREAKKQVEKAVKQLEDKV
J8                QAEDKVKQSREAKKQVEKALKQLEDKVQ
J9                 AEDKVKQLREAKKQVEKALEQLEDKVQL
J14              KQAEDKVKASREAKKQVEKALEQLEDKVK
```

FIGURE 2

VACCINE

This application claims the benefit of provisional U.S. Appln. No. 60/426,409, filed Nov. 15, 2002, and Australian Appln. No. 2002302132, filed Nov. 15, 2002; the entire contents of which are incorporated by reference herein.

FIELD OF INVENTION

The invention relates to vaccines, and in particular to vaccines useful in treatment or prophylaxis of *Streptococcus pyogenes* infection, for example via prevention of colonisation of the throat, for example following intranasal administration.

BACKGROUND TO THE INVENTION

Group A *Streptococcus pyogenes* (GAS) is the most frequent bacterial cause of suppurative infections in humans. *S. pyogenes* usually produce diseases of the skin and respiratory tract, which may lead to serious sequelae like rheumatic fever and glomerulonephritis. GAS results in an estimated 35 million infections each year in the United States of America and Europe. These infections occur predominantly in school-aged children and adolescents, and are mainly present in the upper respiratory tract, resulting in 'Strep throat'. This is not life threatening and usually treatable with antibiotics, however such large numbers of affected puts considerable burden on healthcare resources. A number of complications have been reported to occur subsequent to the primary infection, including in some cases invasive, life threatening diseases. GAS infections cause a variety of clinical conditions, ranging from uncomplicated pharyngitis and pyoderma to the less common, more serious deep tissue infections and streptococci toxic shock syndrome. Untreated Strep pharyngitis may trigger acute rheumatic fever (ARF) which is a serious sequelae of GAS and has had a remarkable resurgence in the developing countries within the last 10 years. In addition, the incidence of ARF has remained high and rheumatic carditis remains the leading cause of heart disease in children around the world.

*S. pyogenes* express one or more surface-associated fibrillar proteins, called M proteins, which are the major virulence factor conferring bacterial resistance to phagocytosis. Antibodies (Abs) directed against these M proteins have been demonstrated to mediate immunity to GAS.

There are currently more than 100 different antigenically distinguishable M proteins. The most severe types of *S. pyogenes* infections have been reported to be associated with M1 and M3 serotypes although other strains are also responsible. The M-types can be loosely classified into rheumatogenic and non-rheumatogenic strains. The M proteins belong to a large family of structurally related proteins which includes the Emm, Enn and Mrp proteins. The M proteins have affinity for several plasma proteins, including fibrinogen, IgG, IgA, complement factor H (fH), factor H like protein 1 (FHL-1) and C4 binding protein (C4BP). It has been suggested that bacterial binding of these plasma proteins contributes to the anti-phagocytic properties displayed by most M proteins.

*S. pyogenes* is a potent activator of the complement system. Binding of complement regulatory proteins by streptococcal M proteins could contribute to the inhibition of C3 deposition on the streptococcal surface, providing a mechanism by which M proteins protect the bacteria from phagocytosis by the polymorphonuclear leukocytes (PMN) which accumulate during inflammation. The interaction between fH and M proteins represents the paradigm of how M proteins protect bacteria from complement attack and phagocytosis.

Current vaccine strategies focus on the outer membrane M proteins, due to their ability to confer resistance to phagocytosis. The M proteins may also induce harmful host immune responses through their ability to induce cross-reactive antibody and T cell responses in humans. Added to the variability and number of these proteins, the development of an effective vaccine against a variety of serotypes has been problematic. Although opsonic antibodies directed against the N terminus of the M protein are mainly responsible for serotype immunity, more than 100 serotypes exist. An effective vaccine would provide a cost effective means of preventing disease and help reduce the increased incidence of microbial antibiotic resistance (in other bacteria) which occurs from over dependence on antibiotic therapies.

The most significant impediment to the use of synthetic peptides as vaccines (parenteral delivery) has been that they are only weakly or non-immunogenic when injected by themselves into animals. This property has necessitated the use of carriers, usually large highly immunogenic proteins to which the peptides are covalently coupled. Selecting a carrier protein for peptide vaccines is problematic. The well known and widely used Tetanus and Diphtheria toxoids are both associated with carrier suppression in adults because of prior immunisation with proteins that are routinely administered alone (eg tetanus). Besides insufficient titres against the various peptides, the development of the conjugates can be both expensive and time consuming.

Since the upper respiratory tract represents the port of entry for GAS-infection, the elicitation of an efficient mucosal response is desirable. It is known that the local IgA response plays a critical role in the elicitation of protective immunity against GAS. In general, it is difficult to induce a secretory, and also systemic, immunity when using the mucosal route for a subunit (peptide) vaccine without added adjuvant.

SUMMARY OF THE INVENTION

The present inventors have demonstrated that effective stimulation of immune responses can be achieved through the use of a group A Streptococcal antigen combined with proteosome adjuvant, in particular for intranasal administration. Thus, in accordance with the present invention, there is provided a vaccine composition comprising at least one group A streptococcal antigen and proteosome adjuvant. The vaccine compositions of the invention are provided for use in inducing an immune response in an individual, for the treatment or prophylaxis of group A streptococcal infection in an individual, preferably via prevention or reduction of colonisation of the throat following intranasal administration.

The invention also provides a method of treatment or prophylaxis of group A Streptococcus comprising administering a vaccine composition of the invention, preferably by intranasal administration to prevent colonisation of the throat.

In a preferred embodiment, the peptide antigens for use in vaccine compositions according to the present invention are highly conserved regions of M proteins of *S. pyogenes*. However, other group A Streptococcal antigens may be used such as peptides derived from MtsA and protein H, such as APP. The vaccine compositions of the present invention are particularly useful for intranasal administration for example, to stimulate a mucosal immune response and/or to inhibit bacterial colonisation of the throat by group A *Streptococci*.

DESCRIPTION OF THE FIGURES

FIG. 2: Sequence of J14 Peptide (SEQ ID NOS:5-15)

DETAILED DESCRIPTION OF THE INVENTION

The present invention relates to vaccine compositions which make use of group A Streptococcal antigens combined with proteosome adjuvant.

Any suitable group A Streptococcal antigen or combination of antigens may be used. Antigenic peptides for administration in vaccine compositions of the invention include peptides derived from M proteins of *S. pyogenes*, peptides derived from protein H and in particular the APP peptide and peptides derived from MtsA. However, any suitable *S. pyogenes* antigenic peptide can be used in accordance with the present invention.

A peptide antigen for use in accordance with the present invention preferably has an amino acid sequence comprising an epitope from an *S. pyogenes* protein. Such peptide comprises at least 6 amino acids, and is preferably 10, 15, up to 20, 30, 40 or 50 amino acids in length. Preferably, the peptide has a sequence identical to a portion of a naturally occurring *S. pyogenes* protein. However, amino acid substitutions may be made, for example, from 1, 2 or 3 up to 10 substitutions, depending on the length of the antigenic sequence. Preferably, the antigenic peptide will have at least 80%, for example at least 85%, 90% or 95% amino acid identity over the entire length of the fragment. Conservative substitutions may be made, for example, according to the following table. Amino acids in the same block in the second column and preferably in the same line in the third column may be substituted for each other.

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In all cases, the peptides of the present invention generate an immune response useful in the treatment or prophylaxis of *S. pyogenes* infection.

Figure 1:
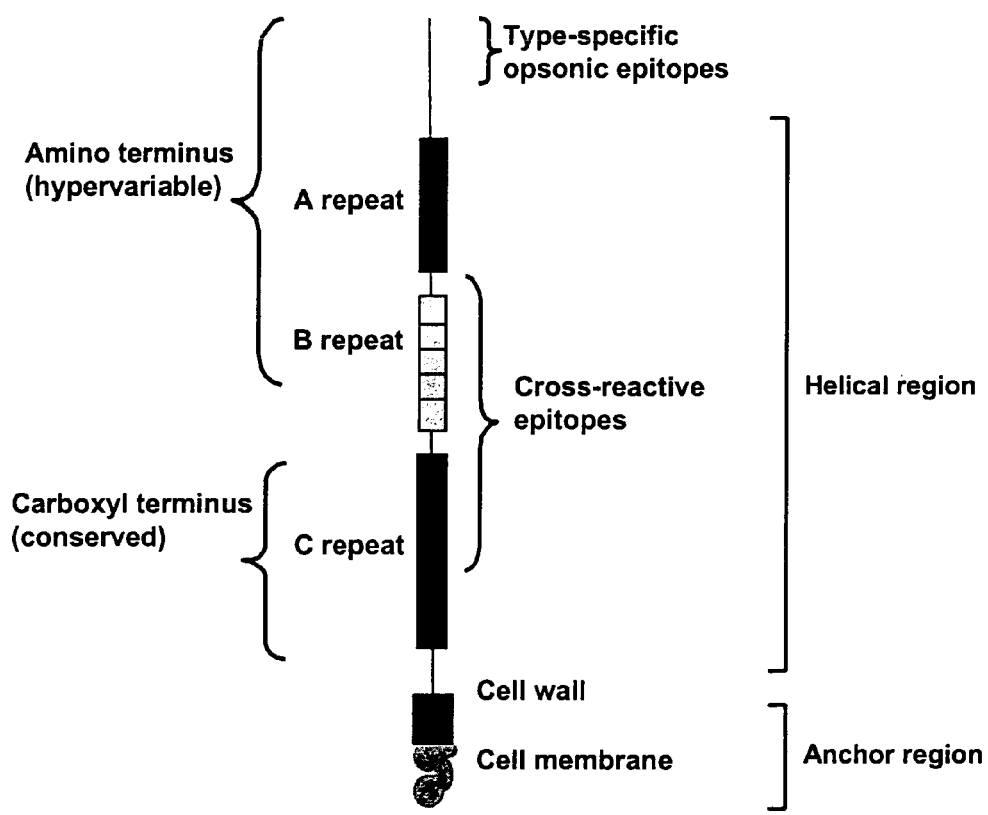
FIG. 1: Diagrammatic representation of the Streptococcal M protein

In one preferred embodiment of the present invention, the antigenic peptide comprises an amino acid sequence from an M protein of *S. pyogenes*. There are a number of different sero types of M protein. Preferably, the antigenic peptide has an amino acid sequence of a fragment of the more prevalent serotypes. The vaccine composition can be selected as appropriate depending on the prevalence of particular sero types in the local area where the population is to be immunised. In one aspect, the peptide antigen is derived from M1 or M3 S. pyogenes serotypes. Although the sequence of M proteins varies between different strains, the M proteins have a generally conserved region. FIG. 1 sets out a diagrammatic representation of S. pyogenes M protein. Preferably, an antigenic peptide for use in accordance with the present invention has an amino acid sequence identical to or derived from a portion of the carboxy terminus conserved region of M proteins. Preferably, the antigenic peptide will demonstrate cross-reactivity between different S. pyogenes serotypes. A particularly preferred sequence in accordance with the present invention comprises the antigen ASREAKKQVEKALE (SEQ ID NO:1).

The antigenic peptide may be flanked by peptide sequences, for example, in the case of helical antigens derived from the carboxyl terminus of M proteins, to maintain the helical conformation of the antigen in the vaccine composition. The flanking sequences may be derived from the same M protein as the antigen, other M proteins or other proteins have a helical structural. Alternatively suitable flanking peptide sequences can be designed to maintain the helical conformation of the antigen. An example of a peptide having suitable flanking sequences has the sequence KQAEDKVKASREAKKQVEKALEQLEDKVK (SEQ ID NO:2).

S. pyogenes peptide antigen for use in accordance with the present invention is preferably selected to avoid potential cross reactivity with human proteins and in particular human keratin. Preferably, a minimal antibody epitope is selected which does not include T cell epitopes having undesirable cross reactivity.

A vaccine composition in accordance with the present invention may incorporate more than one peptide antigenic sequence. In particular, it may be desirable to incorporate more than one S. pyogenes peptide antigens having sequences of fragments of more than one M protein, each optionally provided with flanking sequences as described above. Other suitable S. pyogenes antigens may also be incorporated into a vaccine according to the present invention. Such antigenic peptides may be derived from MtsA or protein H and may be used in place of or in addition to the antigenic peptides having sequences derived from M proteins. MtsA has been shown to be present in a number of S. pyogenes strains, and demonstrates high amino acid identity between strains. Preferably, an antigenic peptide has the sequence of a portion of the N-terminal region of MtsA and more preferably is EIN19, EINTEEEGTPDQISSLIEK (SEQ ID NO:3).

Protein H is an M-like protein derived from the strain AP1. An antigenic sequence derived from protein H is preferably, for example, APP as described in more detail in PCT/GB99/01104. More preferably the peptide is KQL30 having the sequence KQLEDRVQQLETEKQISEASRK-SAEDKVKQ (SEQ ID NO:4). Suitable antigenic determinants of M proteins are described in more detail in WO 96/11944. MtsA is described in more detail in PCT/GB99/04445.

The present invention may also be used for multivalent vaccine, comprising an S. pyogenes peptide antigen, proteosome adjuvant and one or more additional antigens against which it is desired to generate an immune response, such as a bacterial antigen or viral antigen.

An antigenic peptide for use in the invention may be prepared as a fragment of an isolated protein of S. pyogenes. Preferably however, a peptide for use in the invention is made synthetically or by recombinant means. The amino acid sequence of a peptide for use in the invention may be modified to include non-naturally occurring amino acids or to increase the stability of the compound. When the peptide is produced by synthetic means, such amino acids may be introduced during production. The peptide may also be modified following either synthetic or recombinant production.

The peptide for use in the invention may also be produced using D-amino acids. In such cases the amino acids will be linked in reverse sequence in the C to N orientation. This is conventional in the art for producing such peptides.

A number of side chain modifications are known in the art and may be made to the side chains of the peptide for use in the present invention. Such modifications include, for example, modifications of amino acids by reductive alkylation by reaction with an aldehyde followed by reduction with $NABH_4$, amidination with methylacetimidate or acylation with acetic anhydride.

A peptide for use in the invention can be produced in large scale following purification by high pressure liquid chromatography (HPLC) or other techniques after recombinant expression as described below.

Polynucleotides to produce an antigenic peptide for use in the invention may comprise DNA or RNA. They may also be polynucleotides which include within them synthetic or modified nucleotides. A number of different types of modification to polynucleotides are known in the art. These include methylphosphate and phosphorothioate backbones, addition of acridine or polylysine chains at the 3' and/or 5' ends of the molecule.

Although in general the techniques mentioned herein are well known in the art, reference may be made in particular to Sambrook et al, 1989.

An antigenic peptide for use in the present invention is preferably produced by recombinant means by providing a polynucleotide encoding the peptide, and where appropriate encoding any desired flanking sequences, under the control of a promoter and other required sequences. Such a polynucleotide is generally provided in the form of an expression vector.

Such vectors may be transformed into a suitable host cell to provide for expression of a polypeptide of the invention. Thus, a polypeptide for use according to the invention can be obtained by cultivating a host cell transformed or transfected with an expression vector as described above under conditions to provide for expression of the polypeptide, and recovering the expressed polypeptide.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Promoters and other expression regulation signals may be selected to be compatible with the host cell for which the expression vector is designed.

Host cells transformed (or transfected) with the polynucleotides or vectors for the replication and expression of polynucleotides of the invention will be chosen to be compatible with the said vector and preferably will be bacterial such as E.coli. Alternatively they may be cells of a human or animal cell line such as CHO or COS cells, or yeast or insect cells. The cells may also be cells of a non-human animal such as a sheep or rabbit or plant cells.

The vaccine compositions of the present invention also comprise a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant.

The use of proteosome adjuvant has been described in the prior art and is reviewed by Lowell GH in "New Generation Vaccines", Second Edition, Marcel Dekker Inc, New York, Basel, Hong Kong (1997) pages 193-206. Proteosome adjuvant vesicles are described as comparable in size to certain viruses which are hydrophobic and safe for human use. The review describes formulation of compositions comprising non-covalent complexes between various antigens and proteosome adjuvant vesicles which are formed when solubilizing detergent is selectably removed using exhaustive dialysis technology.

Figure 3:
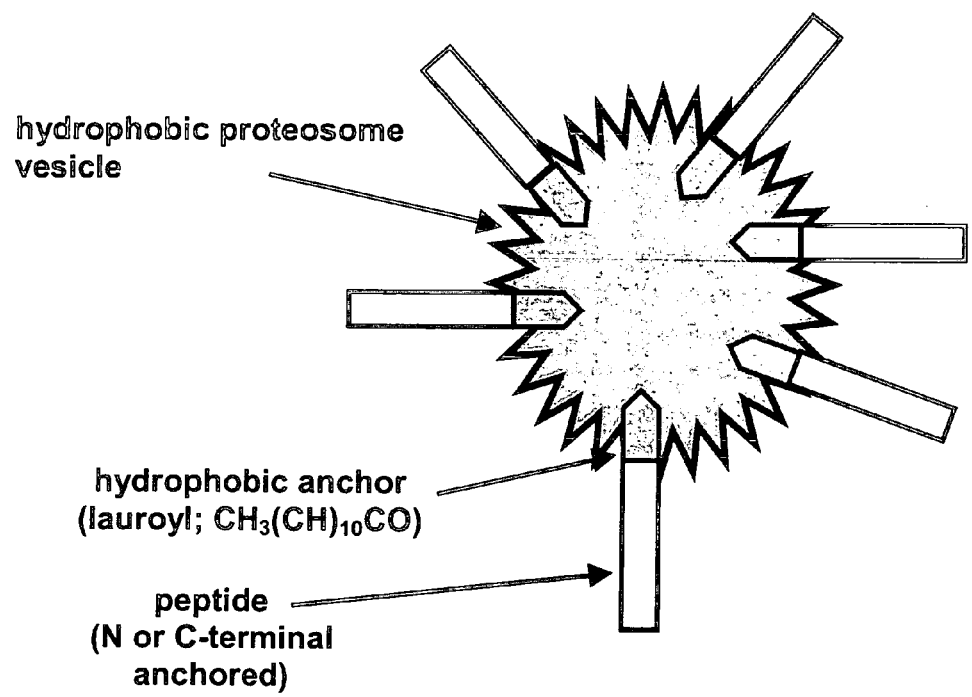
FIG. 3: Illustration of a proteosome adjuvant vesicle

The antigens of the present invention are preferably complexed to the proteosome antigen vesicles through hydrophobic moieties. Typically, an antigen is conjugated to a lipid moiety such as a fatty acyl group. Such a hydrophobic moiety may be linked directly to the peptide antigen or alternatively, a short spacer, for example, of two, three or four, up to six or ten amino acids can be used to link the antigenic peptide to the fatty group. This hydrophobic anchor interacts with the hydrophobic membrane of the proteosome adjuvant vesicles, while presenting the generally hydrophilic antigenic peptide as shown diagramatically, for example, in FIG. 3.

In particular, a hydrophobic anchor may comprise a fatty acyl group attached to the amino terminus or near the carboxyl terminus of the peptide antigen. One example is the twelve-carbon chain lauroyl ($CH_3(CH)_{10}CO$), although any similarly serving fatty acyl group including, but not limited to, acyl groups that are of eight-, ten-, fourteen-, sixteen-, eighteen-, or twenty-carbon chain lengths can also serve as hydrophobic anchors. The anchor may be linked to the peptide antigen using an immunopotentiating spacer. Such a linker may consist of four amino acids (CYGG (SEQ ID NO: 17) or GGYC (SEQ ID NO: 18)), which may assist in maintaining the conformational structure of the peptide. It is appreciated that for either the amino or carboxyl terminus anchors, using three to six glycine residues as spacers instead of two glycine residues would also function in this manner, and the preferred number of glycine residues may be dependent upon, and relative to, the size and conformation of the antigenic peptide used.

In general, the two components, that is the antigenic peptide and proteosome adjuvant are formulated by mixing of the components in a selected solution of detergent(s) and then removing the detergent(s) by diafiltration/ultrafiltration methods. In general, the ratio of proteosome adjuvant to antigen contained in the composition is preferably greater than 1:1 and may be, for example, 1:2, 1:3, 1:4 up to 1:5, 1:10 or 1:20 (by weight). The detergent-based solutions of the two components may contain the same detergent or different detergents and more than one detergent may be present in the mixture subjected to ultrafiltration/diafiltration. Suitable detergents include Triton, Empigen and Mega-10. Other suitable detergents can also be used. The detergents serve to solubilise the components used to prepare the composition.

Multi-valent vaccines, including more than one type of antigenic peptide can be produced by mixing a number of different antigenic peptides with proteosome adjuvant. Alternatively, two or more proteosome adjuvant/antigenic peptide compositions can be produced and subsequently mixed.

The compositions of the present invention may be administered by any suitable route. The vaccines are preferably formulated for delivery by a mucosal, parenteral or transdermal route. In particular, mucosal delivery routes such as nasal, oral and oropharangeal routes are preferred or parenteral routes such as intramuscular or subcutaneous injection. In a particularly preferred embodiment, the vaccine compositions of the present invention are for intranasal administration. Such intranasal administration is effective in reducing or preventing Streptococcal colonisation of the throat.

Suitable binders and carriers may also be introduced depending on the type of formulation that is provided. Oral formulations typically may include excipients such as, for example, pharmaceutical grades of mannitol, lactose, starch, magnesium steriod, sodium saccharine, cellulose, magnesium carbonate. Typically, vaccination is carried out by intranasal delivery of a liquid or spray.

The vaccines are administrated in a manner compatible with the dosage formulation in such an amount as will be prophylactically effective. The quantity to be administered, which is generally in the range of 5 μg to 100 mg, preferably 250 μg to 10 mg of polypeptide antigen per dose depends on a number of factors. These include the subject to be treated, capacity of the subjects immune system to synthesize antibodies and the degree of protection desired. Precise amounts of active ingredient required to be administered may depend on the judgement of the practitioner.

The vaccine may be given in a single dose schedule or preferably in a multiple-dose schedule. A multiple-dose schedule is one in which a primary course of vaccination may be with 1-10 separate doses, followed by other doses given at subsequent time intervals required to maintain and/or reinforce the immune response, for example, at 1-4 months for a second dose and if needed, a subsequent dose(s) after several months.

The formulations of the present invention are particularly useful in inducing opsonic antibodies in sera and or secretory antibodies in saliva for vaccination against *S. pyogenes*. For example, the vaccine compositions of the present invention may be used to generate IgA, for example in saliva and IgG in serum. Such responses can be generated following intranasal administration.

EXAMPLES

The Examples described below use the peptide J14 and proteosome adjuvant compositions as described below.

Chimeric Peptides (J14) and Proteosome Adjuvant

A helical, non-host cross-reactive peptide from the C terminal region of the M protein was identified displayed with a non-M protein peptide sequence designed to maintain the helical folding and antigenicity, J14.

The sequence of the J14 peptide is as follows:
KQAEDKVKASREAKKQVEKALEQLEDKVK (SEQ ID NO:2)

KQAEDKVKASREAKKQVEKALEQLEDKVK

A hydrophobic anchor consisting of a fatty acyl group was attached to the J14 peptide either at that amino terminus or near the carboxyl terminus. For this example, the twelve-carbon chain lauroyl ($CH_3(CH)_{10}CO$) was used, although any similarly serving fatty acyl group including, but not limited to, acyl groups that are of eight-, ten-, fourteen-, sixteen-, eighteen- or twenty-carbon chain lengths can also serve as hydrophobic anchors. The anchor was further distinguished by being linked to the J14 peptide using an immunopotentiating spacer consisting of four amino acids (CYGG (SEQ ID NO: 17) or GGYC (SEQ ID NO: 18)), which also assisted in maintaining the conformational structure of the J14 peptide. It is appreciated that for either the amino or carboxyl terminus anchors, using three to six glycine residues as spacers instead or two glycine residues would also function in this manner, and the preferred number of glycine residues may be dependent upon, and relative to, the size and conformation of the antigenic peptide used.

Two custom designed anchored peptide constructs were synthesized using known organic chemistry methodologies. The amino-terminal J14 construct (nJ14) consisted of the carboxyl terminus of the anchor covalently linked to the amino terminus of the J14 peptide, resulting in lauroyl-CYGG-J14, where CYGG (SEQ ID NO: 17), as per the single letter designation of amino acids, represents the amino acid sequence cysteine-tyrosine-glycine-glycine. The carboxy-terminal J14 construct (cJ14) consisted of the anchor linked toward, but not at, the carboxyl terminus of the J14 peptide. The cJ14 construct differs significantly from the nJ4 construct. The anchored peptide for the cJ14construct was designed and synthesized so that the anchor and immunopotentiating spacer consisted of the following sequence: (K)-(GGYC-lauroyl) (SEQ ID NO: 19), which represents, as per the single amino acid convention, (lysine)-(glycine-glycine-tyrosine-cysteine-lauroyl). Note that a lysine residue was added to the amino terminus of the J14 peptide in addition to the original carboxyl terminus lysine of the J14 peptide. Furthermore, as indicated by the dash between the (K) and the (GGYC-lauroyl), the -(GGYC-lauroyl) was covalently linked via the epsilon amino group of the side chain of the added carboxyl terminus lysine. This linkage was designed to facilitate anchor function while maintaining the conformational structure of the antigenic peptide. The additional length and unique structure of this construct is considered to have been instrumental in facilitating the immunogenicity of this construct alone and especially in a preferred embodiment which is when it is hydrophobically complexed to proteosome adjuvant vesicles to form the proteosome-(cJ14) vaccine. It is understood that the terms "C-terminal", "C-terminal J14", "cJ14" or other such shorthand nomenclature, when used herein alone or in combination with Proteosome adjuvant vaccines refers to the construct described above.

After formulation the following ratios (proteosome:peptide) for both anchor orientations were obtained (see table 12 for more details):

Proteosome Adjuvant: N-Terminal J14 (nJ14)

Ratio A: 1:2.2

Ratio B: 1:4.1

Proteosome Adjuvant: C-Terminal J14 (cJ14)

Ratio A: 1:1.6

Ratio B: 1:4.6

In addition, the estimated peptide final concentration diluted for delivery was 2 mg/ml for all four vaccines. Therefore each mouse was given a total of 30 μl/immunisation which is equivalent to a total of 60 μg of peptide per immunisation for examples 2 and 3. For example 1, subcutaneous immunisation, each mouse received a total of 30 μg of peptide in the form of ratio A (1:2.2 and 1:1.6 for nJ14 and cJ14, respectively)

Example 1

Subcutaneous Immunisation

The integrity of the conformational structure and immunogenicity of the J14 and J14 anchor candidates were determined.

Peptides, with or without anchors, as described in table 3.2, were emulsified in Complete Freund's adjuvant CFA and administered subcutaneously at the tail base of B10.BR inbred mice. After the primary immunisation, boosts of 30 μg antigen in PBS were given on days 21 and 28. Sera were collected 1 day prior to boosts and 15 days after.

Example 1a

Immunogenicity of the Peptide/Proteosomes Delivered Subcutaneously

Figure 4:
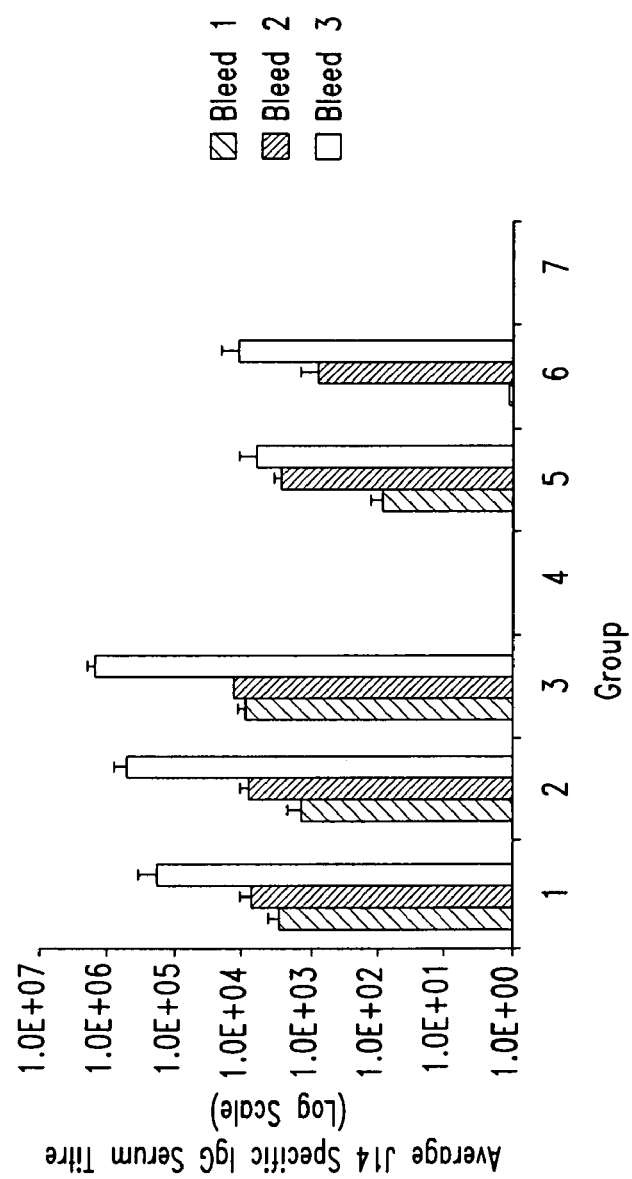
FIG. 4: Graph of average Serum IgG Titre of Bleeds 1, 2 and 3 (J14 Specific Titre) for Example 1 S.E.M is shown.
Group 1 J14 (CFA)—B10.BR—Subcutaneous
Group 2 J14 amino terminal anchor (CFA)—B10.BR—Subcutaneous
Group 3 J14 carboxyl terminal anchor (CFA)—B10.BR—Subcutaneous
Group 4 PBS (CFA)—B10.BR—Subcutaneous
Group 5 J14 amino terminal anchor/proteosome adjuvant (ratio A)—B10.BR—Subcutaneous
Group 6 J14 carboxyl terminal anchor/proteosome adjuvant (ratio A)—B10.BR—Subcutaneous
Group 7 Proteosome adjuvant only—B10.BR—Subcutaneous

Antibody titres, specific for the J14 peptide, are shown in FIG. 4. The antibody titres, after a primary immunisation in CFA and two boosts in PBS (groups 1-3), indicate that the J14 peptide with the addition of either the amino terminal (group 2) or carboxyl terminal (group 3) anchors, have resulted in sera that is able to recognise the standard chimeric J14 peptide. This infers that the addition of either the amino terminal or carboxyl terminal anchor did not disrupt the conformational structure of the J14 chimeric peptide.

TABLE 1

Murine Groups for Example 1.

| Group Number | Immunogen | Immunisation Route | Number of Mice |
|---|---|---|---|
| 1 | J14 (CFA) | S/C | 5 |
| 2 | J14 amino terminal anchor (CFA) | S/C | 5 |
| 3 | J14 carboxyl terminal anchor (CFA) | S/C | 5 |
| 4 | PBS (CFA) | S/C | 5 |
| 5 | J14 amino terminal anchor/ proteosome adjuvant (ratio A) | S/C | 5 |
| 6 | J14 carboxyl terminal anchor/ proteosome adjuvant (ratio A) | S/C | 5 |
| 7 | Proteosome adjuvant only | S/C | |

The subcutaneous immunisation of the peptide-proteosome adjuvant constructs resulted in average titres of 6,160 for group 5 and 11,380 for group 6 (amino and carboxyl terminal J14 anchor formulated with proteosomes-ratio A, respectively). All mice responded to the immunisation schedule after the second boost with titres of the individual mice ranging from 400 to 25,600 for group 5 and 100 to 51,200 for group 6. Neither the CFA or Proteosome adjuvant only immunised mice induced a J14 specific response.

The first three groups using CFA as the adjuvant induced a strong immunological response in all of the mice in those groups. As expected, the PBS/CFA group did not induce a J14 specific response. Groups 5 and 6, utilising the proteosome technology, did induce a response.

Example 1b

Opsonic Potential of Sera from Immunised Mice

Figure 5:
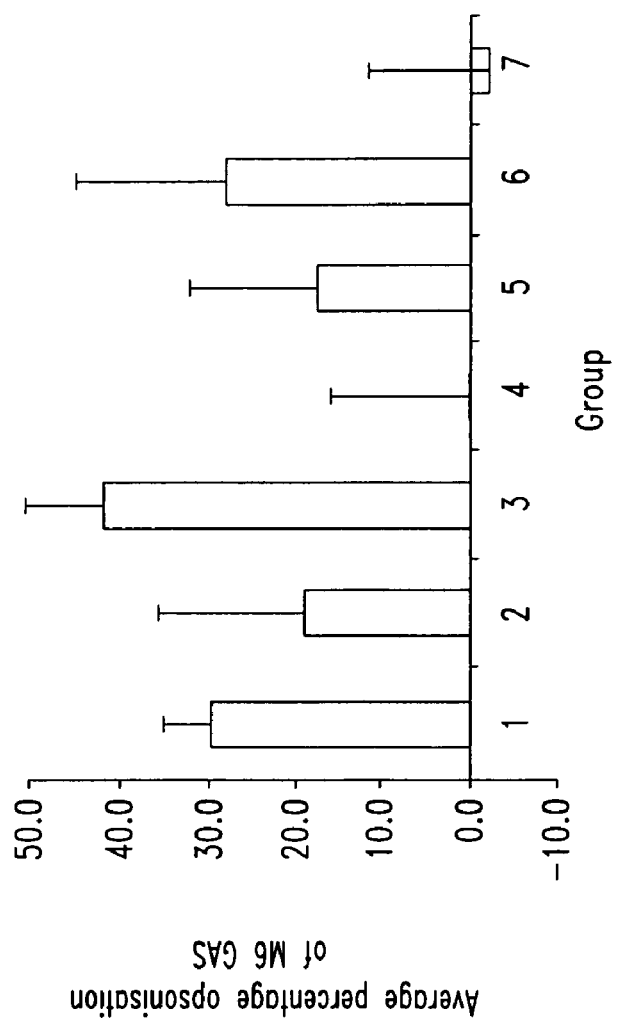
FIG. 5: Graph of average opsonic potential of the sera for the seven groups in Example 1.
Group 1 J14 (CFA)—B10.BR—Subcutaneous
Group 2 14 amino terminal anchor (CFA)—B10.BR—Subcutaneous
Group 3 J14 carboxyl terminal anchor (CFA)—B10.BR—Subcutaneous
Group 4 PBS (CFA)—B10.BR—Subcutaneous
Group 5 J14 amino terminal anchor/proteosome adjuvant (ratio A)—B10.BR—Subcutaneous
Group 6 J14 carboxyl terminal anchor/proteosome adjuvant (ratio A)—B10.BR—Subcutaneous
Group 7 Proteosome adjuvant only—B10.BR—Subcutaneous

Sera were tested for their ability to opsonise or kill the M1 GAS reference strain (FIG. 5). All of the mice in groups one and three opsonised the GAS strain, with killing ranging from 18 to 43% and 22 to 62%, respectively. For group two only 3 of 5 mice opsonised the M1 GAS.

Both of the J14/proteosome adjuvant immunised groups (five and six) opsonised the GAS strain. However, the opsonic potential of the individual mice varied with only 2 out of 4 mice from group five (mouse number 4 died before the opsonisation assay) and 3 out of 5 mice opsonising the bacteria from group six. Both of the control groups (four and seven) did not kill the bacteria in the in vitro assay.

Discussion and Conclusions

The experiment showed that sera raised to the peptides containing the anchors was able to recognise the standard J14 chimeric peptide and therefore the anchors did not appear to disrupt the conformational structure of the peptide. It was also shown the peptide proteosome adjuvant constructs were able to induce an immune response to the J14 peptide, however it was not as strong as that of J14 when combined with CFA.

Example 2

Nasal Immunisation with Intraperitoneal Challenge

The immunogenicity of the J14 peptide/proteosome adjuvant was determined in the murine model. The potential of intranasal immunisation with the vaccine candidate and degree of protection inferred against intraperitoneal challenge were determined. Peptides complexed with proteosome adjuvant according to table 2 were used for intranasal immunisation of Quackenbush (outbred) derived from Swiss outbred mice. Two boosts of 60 µg peptide/30 µl/mouse at 21 day intervals, followed the primary immunisation. One day prior to the boosts and 15 days after serum IgG titres specific for J14 were measured and isotyping performed. IgA titres from salivations collected 2 days prior and 14 days after boosts were determined. Mice were intraperitoneally challenged with a dose of M1 GAS reference strain.

TABLE 2

Murine Groups for Example 2

| Group Number | Immunogen | Immunisation Route | Number of Mice |
|---|---|---|---|
| 1 | J14 amino terminal anchor | I/N | 10 |
| 2 | J14 amino terminal anchor/ proteosome adjuvant (ratio A) | I/N | 15 |
| 3 | J14 amino terminal anchor/ proteosome adjuvant (ratio B) | I/N | 15 |
| 4 | J14 carboxyl terminal anchor | I/N | 10 |
| 5 | J14 carboxyl terminal anchor/ proteosome adjuvant (ratio A) | I/N | 15 |
| 6 | J14 carboxyl terminal anchor/ proteosome adjuvant (ratio B) | I/N | 15 |
| 7 | Proteosome adjuvant only | I/N | 10 |
| 8 | PBS | I/N | 15 |

Example 2a

Immunogenicity of the J14/Proteosome Adjuvant Constructs

Figure 6:
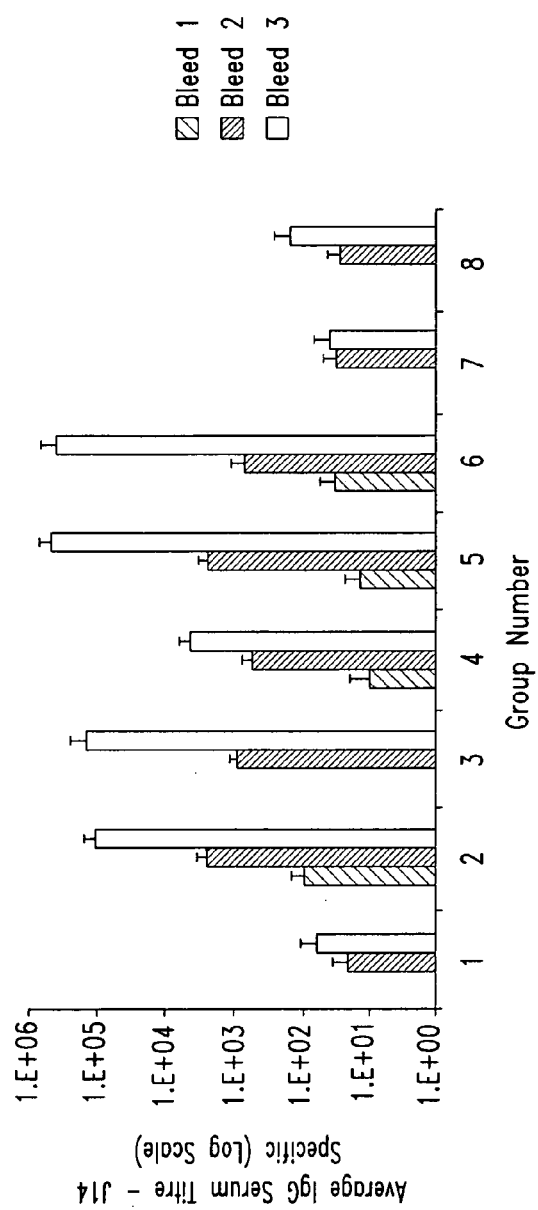
FIG. 6: Average J14 specific serum IgG for the three bleeds for Example 2.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

Total IgG antibody titres, specific for the J14 peptide, are shown in FIG. 6. Groups 2,3,5 and 6 (peptide-proteosome adjuvant groups) also induced significant J14 specific serum antibody titres. Overall, the average titres of the control groups (7 and 8) were not significant compared to the J14—adjuvant groups in the final bleed. Approximately one third of group 4 (mice immunised with the carboxyl terminal anchored J14) induced antibodies that recognised the J14 peptide.

The response of the control groups given the peptide alone varied. In group 1 none of the mice responded to the peptide. However, for group 4 two mice in particular (mouse numbers four and ten) gave a very strong response to the peptide for all isotypes, therefore accounting for the high average titres observed. The majority of mice from the peptide-proteosome adjuvant formulations immunised groups responded.

Example 2b

Opsonic Potential of Sera from Immunised Mice

Figure 7:
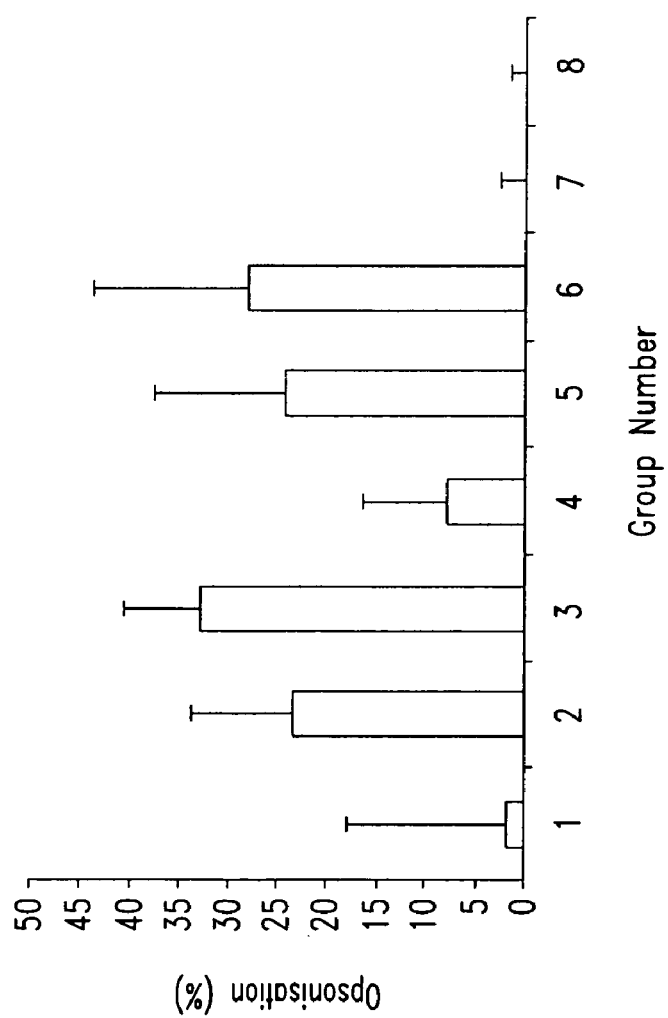
FIG. 7: Graph of average in vitro opsonisation of M1 GAS by serum from the final bleed in Example 2.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

The opsonic potential of serum collected from the final bleed was determined (FIG. 7). As expected groups 7 and 8 did not kill the GAS reference strain in the in vitro assay. The average kill for mice immunised with the N-terminal anchored group was 1.7% and for the C-terminal anchored group average kill was 8%. The proteosome adjuvant immunised groups 2, 3, 5 and 6 averaged greater then 20% opsonisation, however large variability between individual mice was observed.

Example 2c

Peptide/Proteosome Adjuvant Induced Saliva and Faecal IgA

Figure 8:
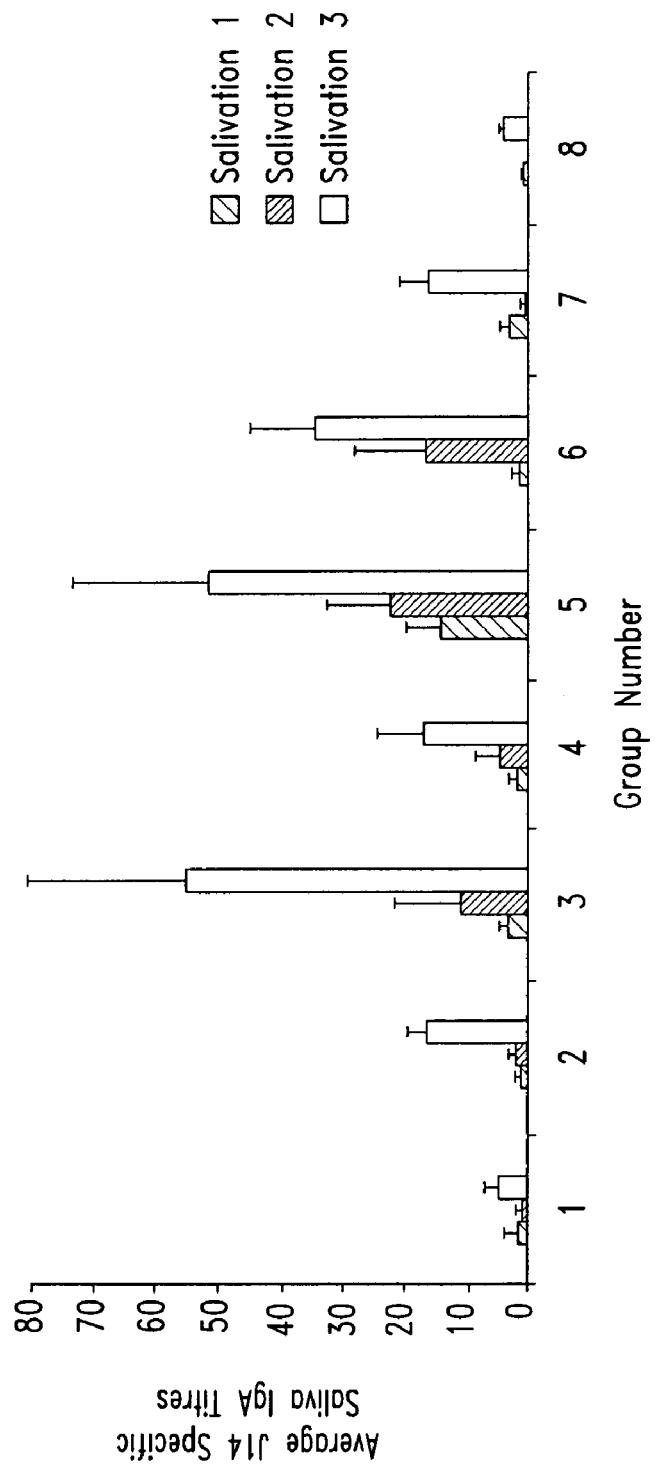
FIG. 8: Graph of average saliva J14 specific IgA for the three salivations taken before challenge for Example 2.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

Saliva was collected after immunisation, 2 days prior to the boosts and 14 days after the final boost. The J14 specific IgA titres were determined as shown in FIG. 8. All of the mice in group one responded with titres ranging from 10 to 80. For group 8, 7 out of 14 mice responded with titres ranging from 0 to 10. The peptide-anchor groups, 1 and 4, had 4/10 and 7/10 mice respond respectively with individual titres ranging from 0 to 20 and 0 to 80. Of the peptide proteosome adjuvant groups 2 (12/15), 3 (11/15), 5 (all responded) and 6 (all responded), titres of the individual mice ranged from 0 to 40, 0 to 640, 10 to 320 and 10 to 160, respectively.

Figure 9:
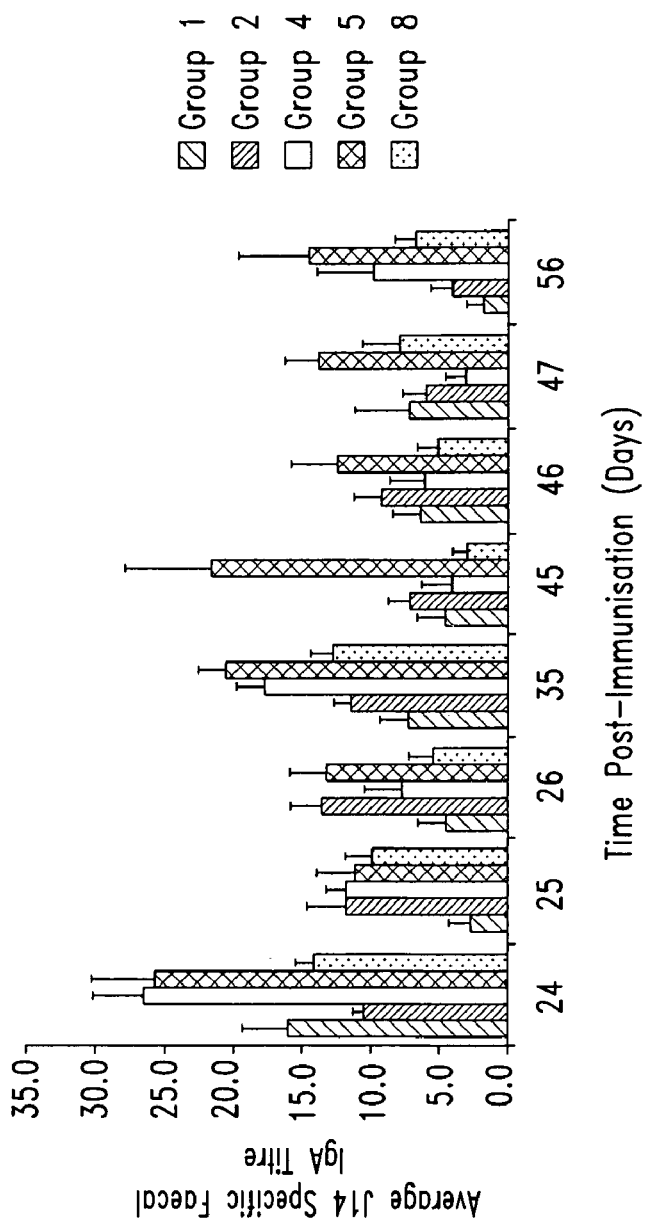
FIG. 9: Graph of average faecal J14 specific IgA titres for groups 1,2,4,5 and 8 prior to challenge in Example 2.
Group 1 J14 amino terminal anchor—Quackenbush—Intranasal
Group 2 J14 amino terminal anchor/proteosome adjuvant (ratio A)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 8 PBS—Quackenbush—Intranasal

Faecal samples were collected on days 24, 25, 26, 35, 45, 46, 47 and 56 post-primary immunisation. The J14 specific IgA titres were determined as shown in FIG. 9. Faecal IgA was detected for the peptide/proteosome adjuvant group 2 and in particular, group 5, with the titres appearing to peak approximately 3 to 4 days after each boost.

Example 2d

GAS Challenge of Immunised Mice

Figure 10:
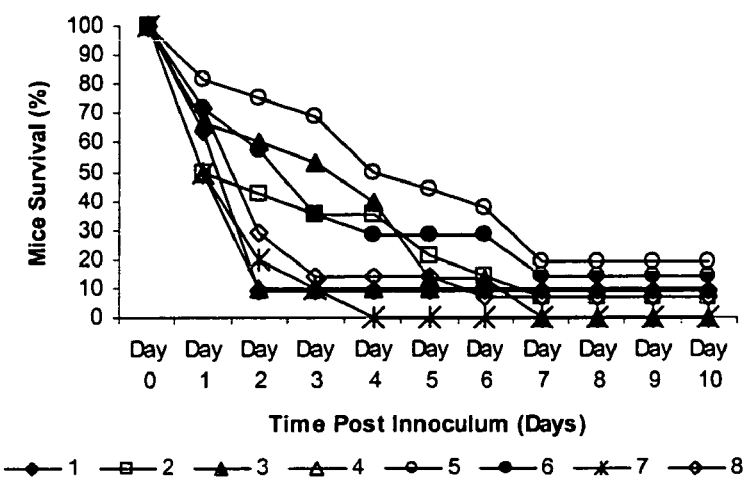
FIG. 10: Graph of mouse survival (%) after challenge with M1 GAS for example 2. All groups are shown.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

A dose curve for each mouse strain was determined for the M1 GAS reference strain. Mice were then challenged with a LD90 dose of the M1 GAS strain calculated from this curve. Following challenge mice were monitored for 10 days for death and morbidity. The results of the GAS challenge are shown in a series of FIGS. 10 to 12.

Figure 11:
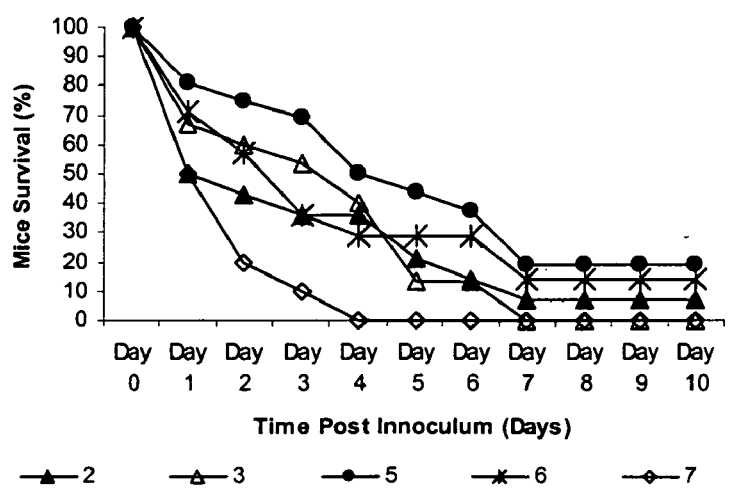
FIG. 11: Graph of mouse survival after challenge with M1 GAS for Example 2. Groups 2, 3, 5, 6 and 7 are shown.
Group 2 J14 amino terminal anchor/proteosome adjuvant (ratio A)—Quackenbush—Intranasal
Group 3 J14 amino terminal anchor/proteosome adjuvant (ratio B)—Quackenbush —Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Figure 12:
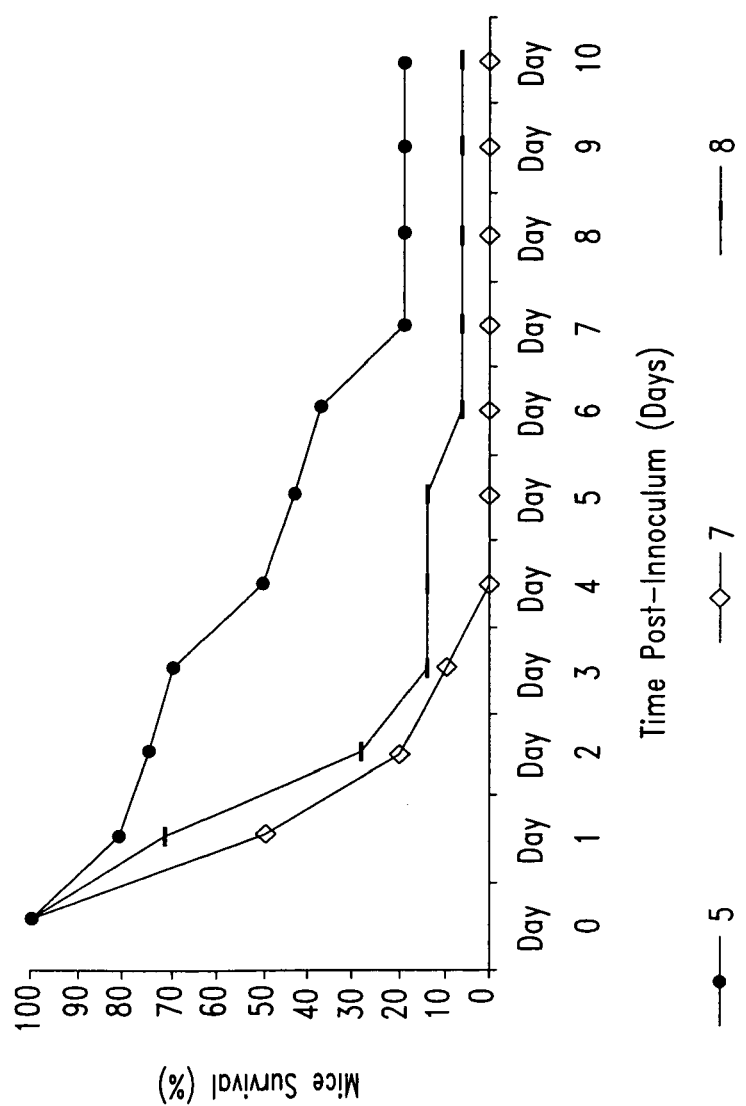
FIG. 12: Graph of mouse survival after challenge with GAS for Example 2. Groups 5, 7 and 8 are shown.
Group 5 J14 carboxyl terminal anchor/proteosome adjuvant (ratio A)—Quackenbush—Intranasal Group 7 Proteosome adjuvant only—Quackenbush—Intranasal
Group 8 PBS—Quackenbush—Intranasal

FIG. 11 shows the results for the peptide-proteosome adjuvant groups (2, 3, 5 and 6). The peptide-proteosome adjuvant appeared to induce a delay in mortality of the mice with these groups. This is clearly demonstrated in FIG. 12, which highlights the difference between group 5 (J14 carboxyl terminal anchor—proteosome adjuvant—ratio A), and group 8 (PBS). Group 5 induced the strongest antibody response of all the peptide-proteosome adjuvant groups. It is proposed that the peptide-proteosome adjuvant constructs reduce the initial bio-burden of the GAS infection, thus delaying in death in these groups. Considering the mice received approximately an LD90 i.p., which rarely occurs in humans.

Discussions and Conclusions

The constructs delivered intranasally induced a strong IgG and IgA antibody response in the serum and saliva, respectively. In addition, it was shown that the serum IgG antibodies were able to opsonise the GAS reference strain in vitro. While not able to induce significant protection in group 5 ($0.05 > P > 0.01$) at day 10 of the challenge (FIG. 12), there was a significant delay in death of the immunised mice for days 2 to 6 post-challenge ($P < 0.05$) compared to the PBS control group (group 8).

The number of surviving mice in group 5 was also significant ($P < 0.05$) compared to the proteosome adjuvant control group 7 up until day 7 post-challenge. Tables 4 and 5 show the days on which there was a significant difference in mice survival between the peptide-proteosome immunised groups (2,3,5 and 6) and the proteosome adjuvant only and PBS control groups (groups 7 and 8, respectively).

TABLE 4

Significance Summary of Mice Survival Post-Challenge Data (Example 2).
P values shown, dark grey $P < 0.05$ and light grey $P < 0.1$.
Groups 2,3,5,6 v 7. (Number of Surviving Mice/Number of Mice Challenged)

| Day | Group 2 proteosome adjuvant: nJ14(1:2.2) | Group 3 proteosome adjuvant: nJ14(1:4.1) | Group 5 proteosome adjuvant: cJ14(1:1.6) | Group 6 proteosome adjuvant: cJ14(1:4.6) | Group 7 proteosome adjuvant only |
|---|---|---|---|---|---|
| 1 | 0.659 (7/14) | 0.337 (10/15) | 0.107 (13/16) | 0.260 (10/14) | -(5/10) |
| 2 | 0.234 (6/14) | 0.058 (9/15) | [shaded] | 0.079 (8/14) | -(2/10) |
| 3 | 0.171 (5/14) | [shaded] | [shaded] | 0.171 (5/14) | -(1/10) |
| 4 | [shaded] | [shaded] | [shaded] | 0.094 (4/14) | -(1/10) |
| 5 | 0.179 (3/14) | 0.350 (2/15) | [shaded] | 0.094 (4/14) | -(0/10) |
| 6 | 0.329 (2/14) | 0.350 (2/15) | 0.215 (3/16) | 0.094 (4/14) | -(0.10) |
| 7 | 0.583 (1/14) | 1.00 (0/15) | 0.215 (3/16) | 0.329 (2/14) | -(0/10) |
| 8 | 0.583 (1/14) | 1.00 (0/15) | 0.215 (3/16) | 0.329 (2/14) | -(0/10) |
| 9 | 0.583 (1/14) | 1.00 (0/15) | 0.215 (3/16) | 0.329 (2/14) | -(0/10) |
| 10 | 0.583 (1/14) | 1.00 (0/15) | 0.215 (3/16) | 0.329 (2/14) | -(0.10) |

TABLE 5

Significance Summary of Mice Survival Post-Challenge Data (Example 2).
P values shown, dark grey $P < 0.05$ and light grey $P < 0.1$.
Groups 2,3,5,6 v 8. (Number of Surviving Mice/Number of Mice Challenged)

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 8 PBS |
|---|---|---|---|---|---|
| 1 | 0.220 (7/14) | 0.550 (10/15) | 0.419 (13/16) | 0.649 (10/14) | — (10/14) |
| 2 | 0.347 (6/14) | 0.092 (9/15) | [shaded] | 0.126 (8/14) | — (10/14) |
| 3 | 0.193 (5/14) | 0.033 (8/15) | [shaded] | 0.192 (5/14) | — (2/14) |
| 4 | 0.193 (5/14) | 0.129 (6/15) | [shaded] | 0.324 (4/14) | — (2/14) |

TABLE 5-continued

Significance Summary of Mice Survival Post-Challenge Data (Example 2).
P values shown, dark grey P < 0.05 and light grey P < 0.1.
Groups 2,3,5,6 v 8. (Number of Surviving Mice/Number of Mice Challenged)

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 8 PBS |
|---|---|---|---|---|---|
| 5 | 0.500 (3/14) | 0.674 (2/15) | 0.086 (7/16) | 0.324 (4/14) | — (2/14) |
| 6 | 0.500 (2/14) | 0.527 (2/15) | 0.353 (3/16) | 0.163 (4/14) | — (1/14) |
| 7 | 0.759 (1/14) | 0.483 (0/15) | 0.353 (3/16) | 0.500 (2/14) | — (1/14) |
| 8 | 0.759 (1/14) | 0.483 (0/15) | 0.353 (3/16) | 0.500 (2/14) | — (1/14) |
| 9 | 0.759 (1/14) | 0.483 (0/15) | 0.353 (3/16) | 0.500 (2/14) | — (1/14) |
| 10 | 0.759 (1/14) | 0.483 (0/15) | 0.353 (3/16) | 0.500 (2/14) | — (1/14) |

Example 3

Nasal Immunisation with Nasal Challenge

The potential of intranasal immunisation with the vaccine candidate and the degree of protection, thus reduction in bio-burden, achieved against intranasal challenge were ascertained in a murine model.

Quackenbush (outbred strain) derived from the Swiss outbred mouse were given two boosts at 21 day intervals after the primary immunisation. 1 day prior to the boosts and 15 days after the final boost before challenge, serum IgG titres were determined. IgA titres were determined for the saliva collected 2 days prior to the boosts and 14 days after the final boost. Faeces were collected as described previously.

Mice were challenged with M1 GAS reference strain (streptomycin resistant) via the nasal route. Post challenge mice were monitored on a daily basis for a period of 15 days. Regular throat swabs were taken of surviving mice to monitor GAS colonisation of the throat on days 1, 2, 3, 6, 9 and 15.

TABLE 3

Murine Groups for Example 3.

| Group Number | Immunogen | Immunisation Route | Number of Mice |
|---|---|---|---|
| 1 | J14 amino terminal anchor | I/N | 10 |
| 2 | J14 amino terminal anchor/ proteosome adjuvant (ratio A) | I/N | 15 |
| 3 | J14 amino terminal anchor/ proteosome adjuvant (ratio B) | I/N | 15 |
| 4 | J14 carboxyl terminal anchor | I/N | 10 |
| 5 | J14 carboxyl terminal anchor/ proteosome adjuvant (ratio A) | I/N | 15 |
| 6 | J14 carboxyl terminal anchor/ proteosome adjuvant (ratio B) | I/N | 15 |
| 7 | Proteosome adjuvant only | I/N | 10 |
| 8 | PBS | I/N | 15 |

Example 3a

Immunogenicity of the Peptide/Proteosome Adjuvant Constructs

Figure 13:
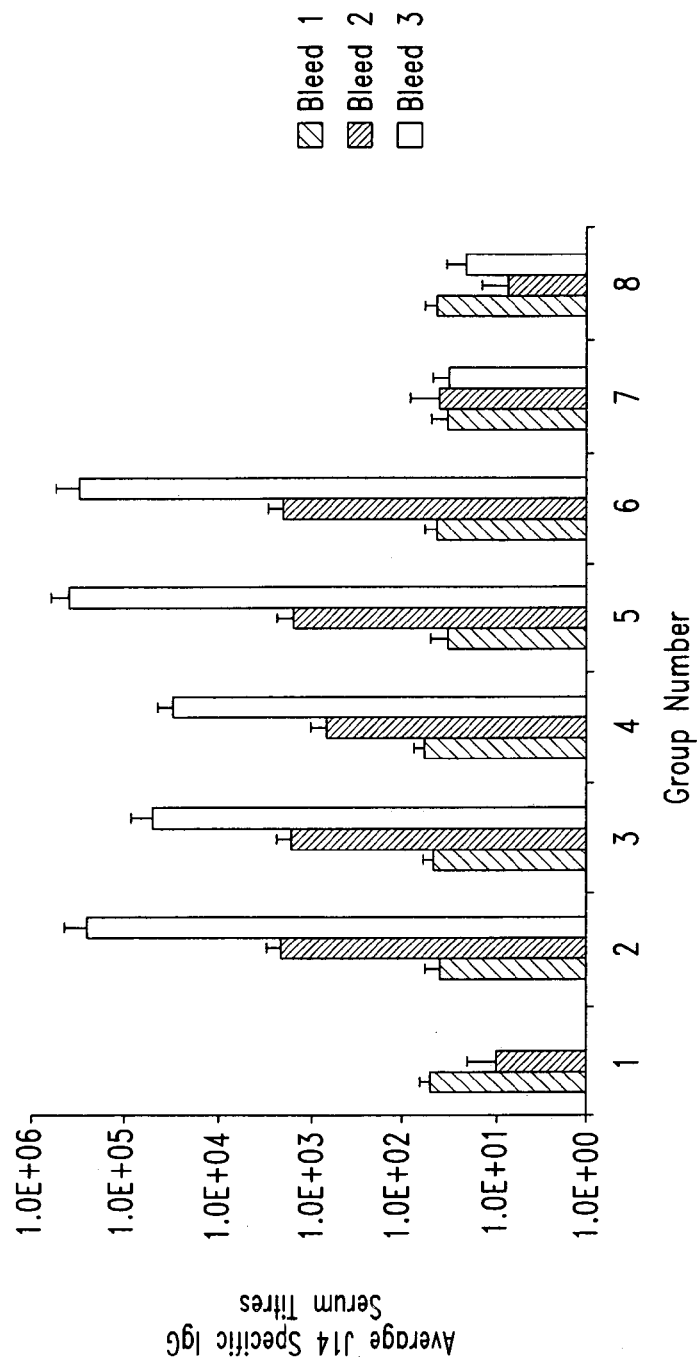
FIG. 13: Graph of serum J14 specific IgG antibody titre murine groups in Example 3.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J4 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

The average serum IgG titre was determined to monitor J14 specific serum antibody titres (FIG. 13). The antibody responses observed (FIG. 13) are similar to those obtained previously with nasal immunisation and intraperitoneal challenge FIG. 6). The average serum IgG isotype titres were determined for the final bleed.

Example 3b

Opsonic Potential of Sera from Immunised Mice

Figure 14:
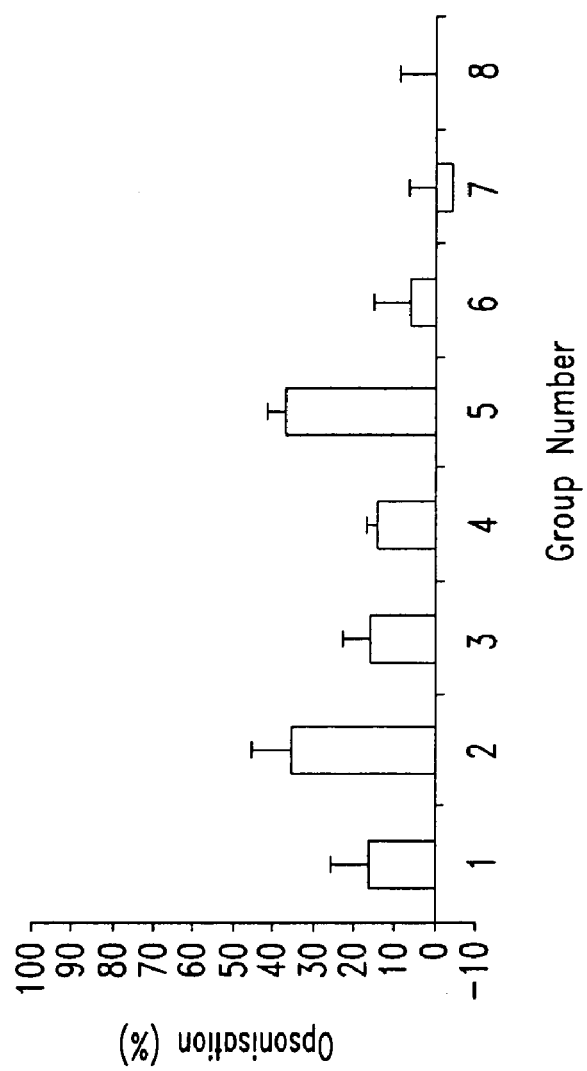
FIG. 14: Graph of the average in vitro opsonisation of the GAS reference strain for the 8 murine groups in Example 3.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

The average opsonic potential of the serum from the final bleed was determined as previously described for the 8 murine groups (FIG. 14).

Example 3c

Figure 15:
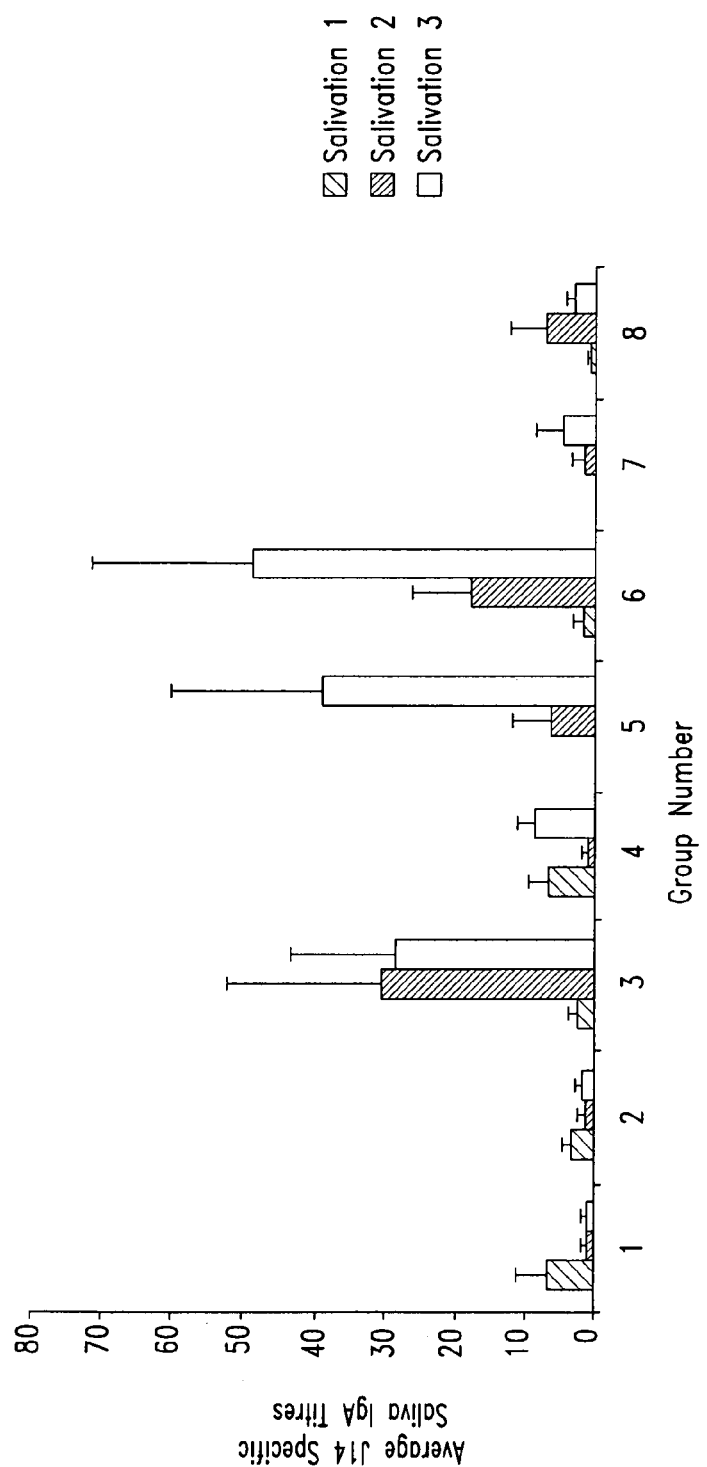
FIG. 15: Graph of average J14 specific IgA titres found the saliva for all of the murine groups in Example 3.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

Detection of Saliva and Faecal IgA Antibodies in Mice Immunised with the Peptide/Proteosome Adjuvant Formulations The average J14 specific IgA titres were determined for the saliva collected at each designated time point for each murine group (FIG. 15). The proteosome adjuvant-immunised groups 3, 5 and 6 gave the strongest saliva IgA responses. A similar trend was observed in the first experiment (FIG. 8).

Figure 16:
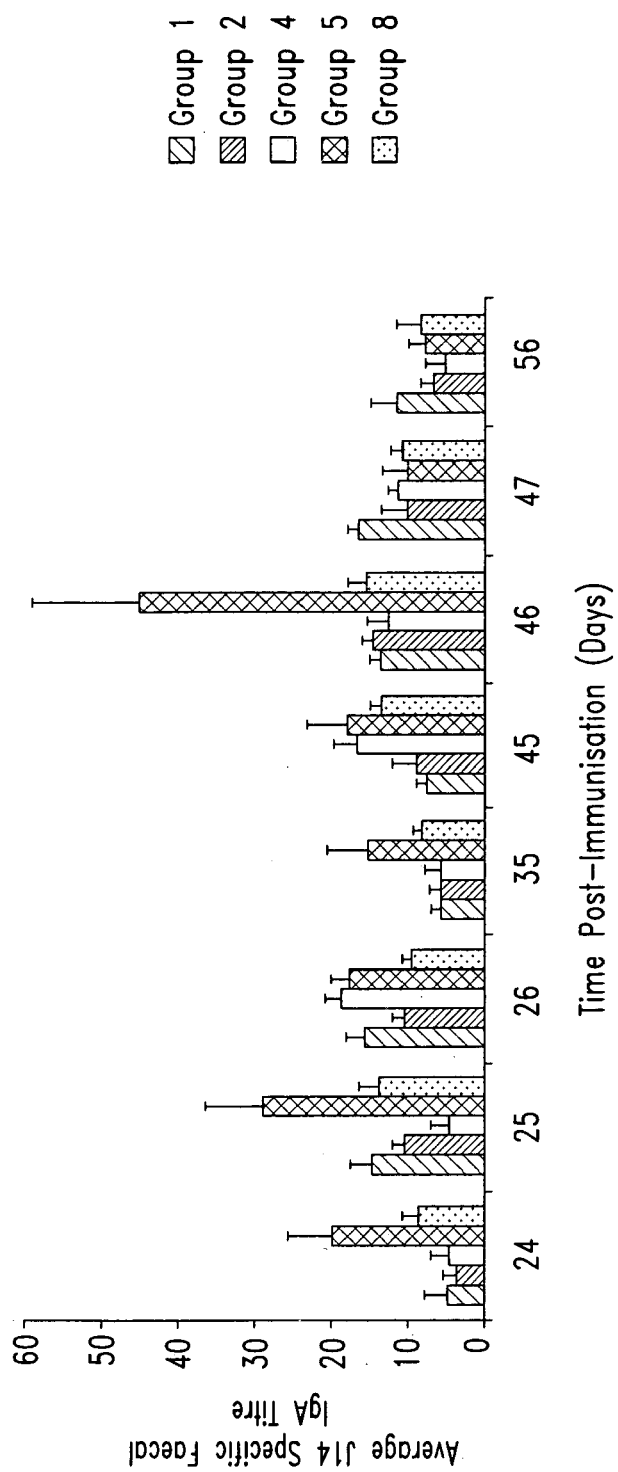
FIG. 16: Graph of average faecal J14 specific IgA titres for groups 1,2,4,5 and 8 prior to challenge in Example 3.
Group 1 J14 amino terminal anchor—Quackenbush—Intranasal
Group 2 J14 amino terminal anchor/proteosome adjuvant (ratio A)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 8 PBS—Quackenbush—Intranasal
Figure 17:
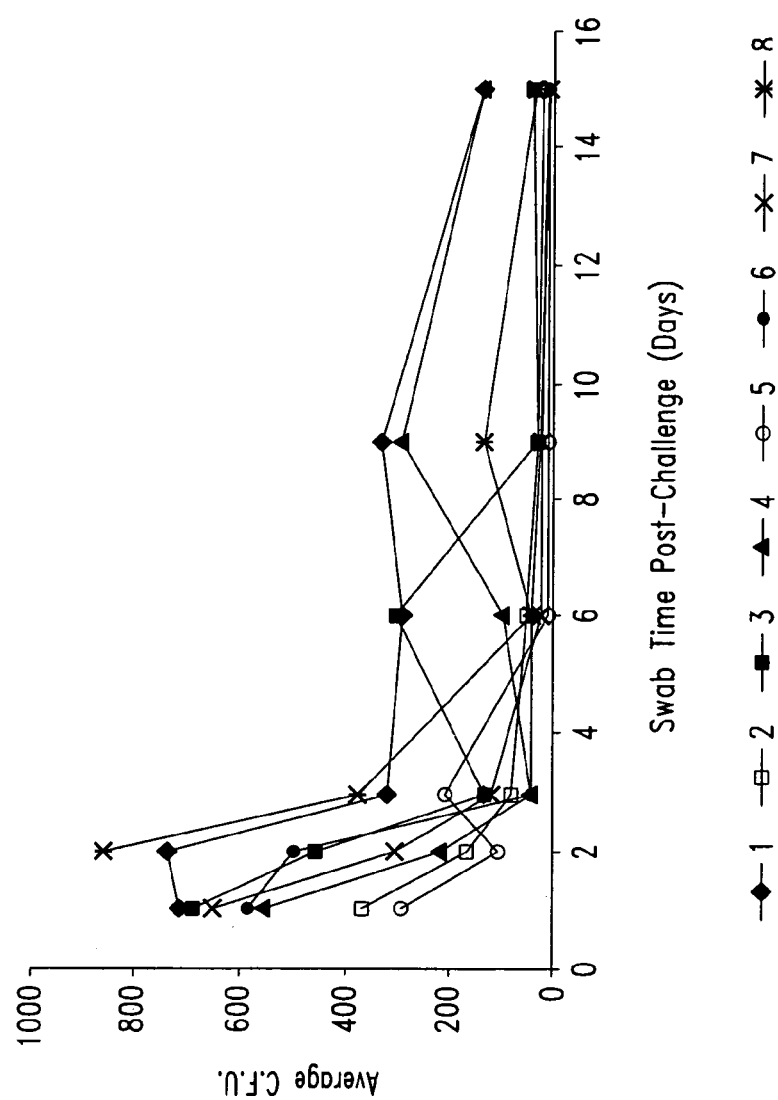
FIG. 17: Average C.F.U. of GAS for each group over the 15 day monitoring period for Example 3. All groups are shown.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

The J14 specific IgA titres of faecal samples were determined as shown in FIG. 16. IgA antibodies were detected in the faecal samples of mice from group 5, with titres appearing to peak 3 to 4 days after boosting (FIG. 16).

Example 4

Intranasal Challenge of Immunised Mice

Following intranasal challenge with GAS, mice were monitored for GAS colonisation of the throat by swabbing on days 1, 2, 3, 6, 9 and 15 post challenge. Data from the throat swabs is presented in four different formats; average colony forming units of GAS, percent positive or dead, percentage of surviving mice, and percent positive of surviving mice.

Example 4a

The Average Colony Forming Units (C.F.U.) of GAS

Figure 25:
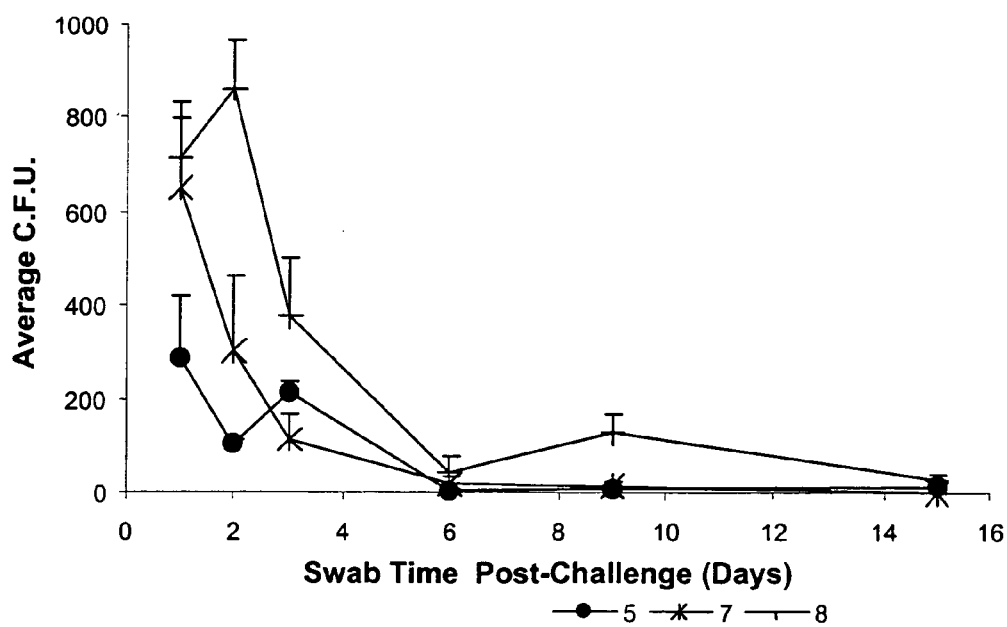
FIG. 25: Graph of the average CFU of GAS for groups 5, 7 and 8 in Example 3.
Group 5 J14 carboxyl terminal anchor/proteosome adjuvant (ratio A)—Quackenbush—Intranasal
Group 7 Proteosome adjuvant only—Quackenbush—Intranasal
Group 8 PBS—Quackenbush—Intranasal

The average C.F.U of GAS was obtained for all surviving mice for each group and the best immunised group shown in FIG. 25, with the corresponding controls.

Figure 18:
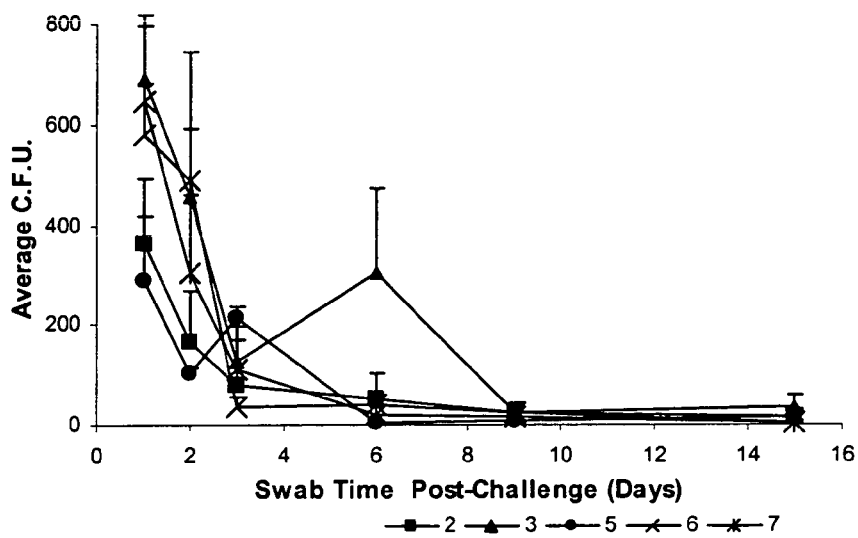
FIG. 18: Graph of average C.F.U. of GAS from throats swabs taken over the 15 day monitoring period for Example 3. Groups 2, 3, 5, 6 and 7 are shown.
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Figure 19:
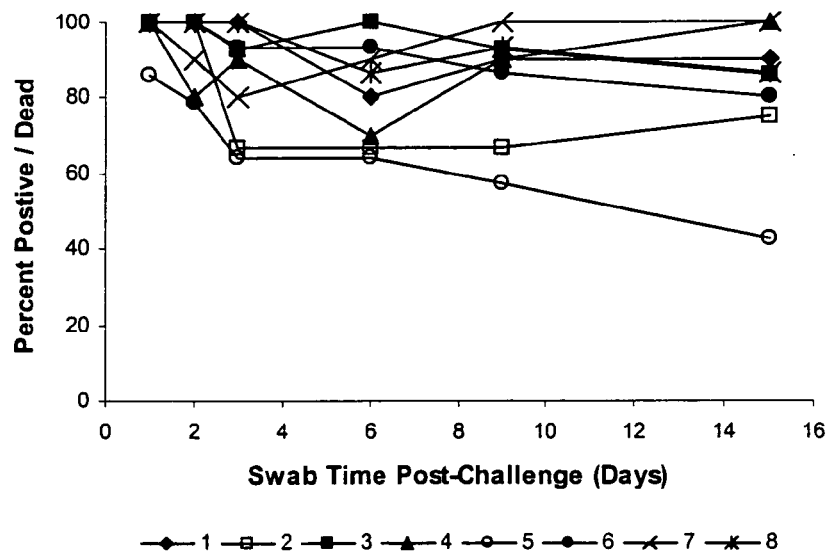
FIG. 19: Graph of the percentage of swab positive or dead mice for the 8 groups Example 3. All groups are shown.
Group J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal

Groups 2 and 5 of the J14 proteosome adjuvant immunised mice (FIG. 18) had lower C.F.U. of GAS compared to the control groups. These two groups practically cleared the GAS colonisation quicker then the PBS control groups by day 6 and maintained this clearance until the end of the monitoring period at day 15. The average C.F.U. for groups 5, 7 and 8 are directly compared in FIG. 25.

Example 4b

Percent Positive or Dead

Figure 20:
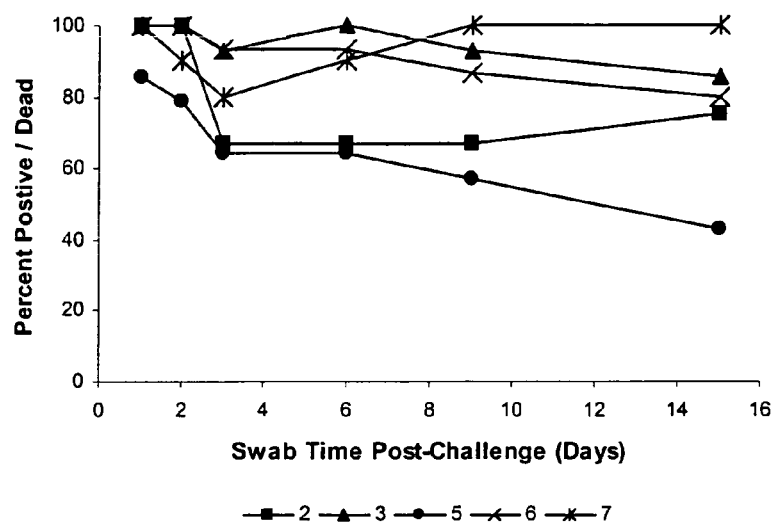
FIG. 20: Graph of the percentage of swab positive or dead mice Example 3. Groups 2, 3, 5, 6 and 7 are shown.
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjucant only—Quackenbush—Intranasal
Figure 21:
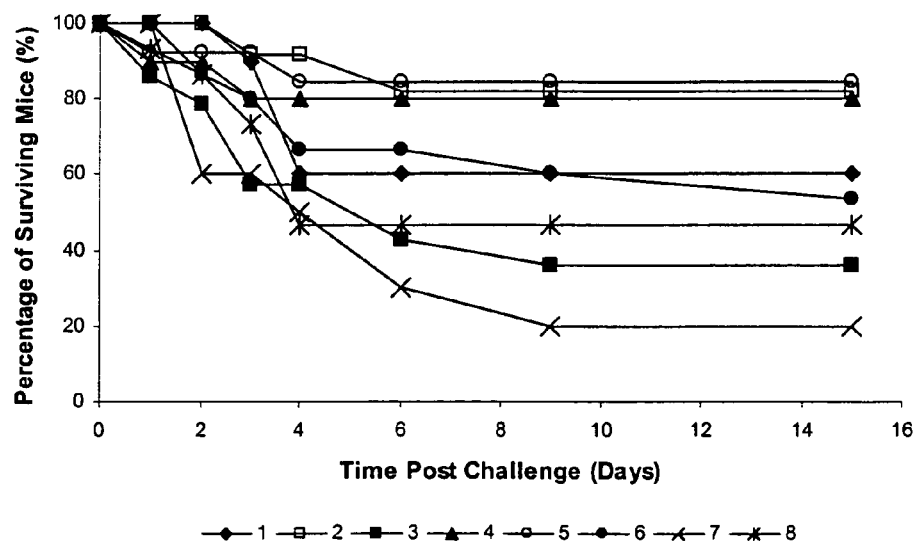
FIG. 21: Graph of the percentage of surviving mice for each of the 8 groups in Example 3. All groups are shown.
Group 1 J14 amino terminal anchor—Quackenbush—Intranasal
Group 2 J14 amino terminal anchor/proteosome adjuvant (ratio A)—Quackenbush—Intranasal Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal
Figure 26:
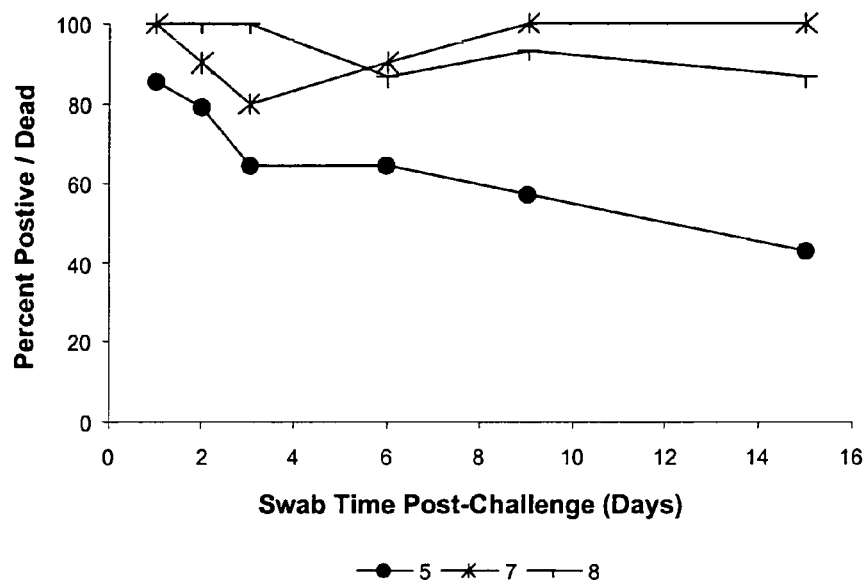
FIG. 26: Graph of the percentage of swab positive or dead mice for groups 5, 7 and 8 for the 15 day monitoring period in Example 3.
Group 5 J14 carboxyl terminal anchor/proteosome adjuvant (ratio A)—Quackenbush—Intranasal
Group 7 Proteosome adjuvant only—Quackenbush—Intranasal
Group 8 PBS—Quackenbush—Intranasal

The percentage of mice in each group which returned a GAS positive swab or were dead was recorded. Spleens from the dead mice were removed and checked for the presence of GAS. Groups 5, 7 (proteosome adjuvant only) and 8 (PBS) are directly compared in FIG. 26. By day 15 all peptide/proteosome adjuvant immunised groups had reduced number of mice either dead or swab positive when compared to the proteosome adjuvant only immunised group (FIG. 20).

Example 4c

Percentage of Surviving Mice

Figure 22:
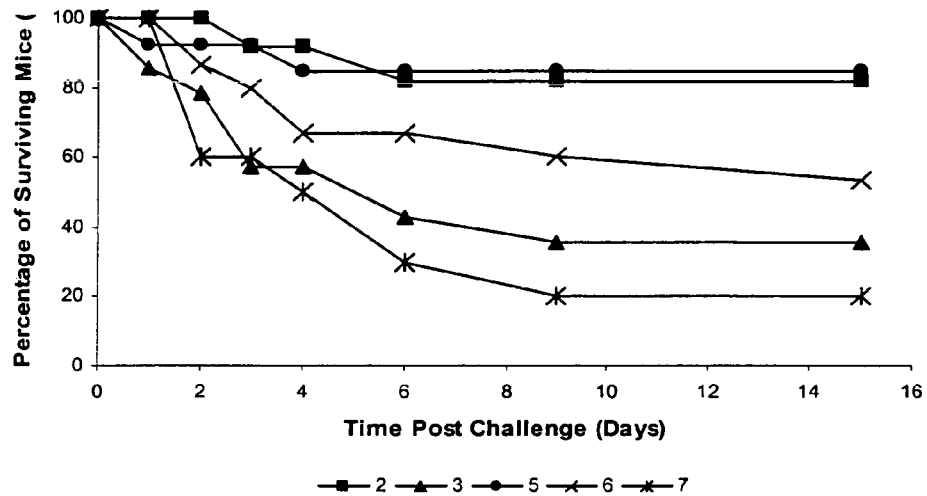
FIG. 22: Graph of the percentage of surviving mice for in Example 3. Groups 2, 3, 5, 6 and 7 are shown.
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Figure 23:
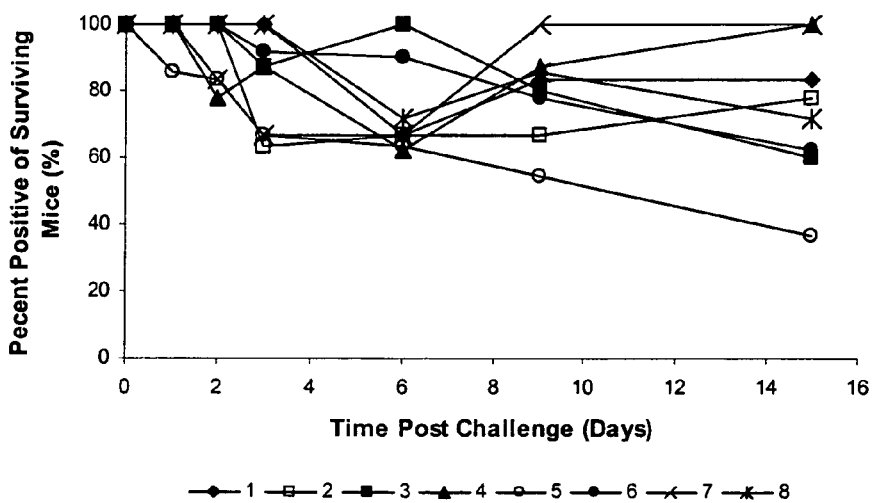
FIG. 23: Graph of the percentage of surviving swab positive mice in each group for Example 3. All groups are shown.
Group 1 J14 amino terminal anchor—Quackenbush—Intranasal
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 4 J14 carboxyl terminal anchor—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal
Group 8 PBS—Quackenbush—Intranasal
Figure 24:
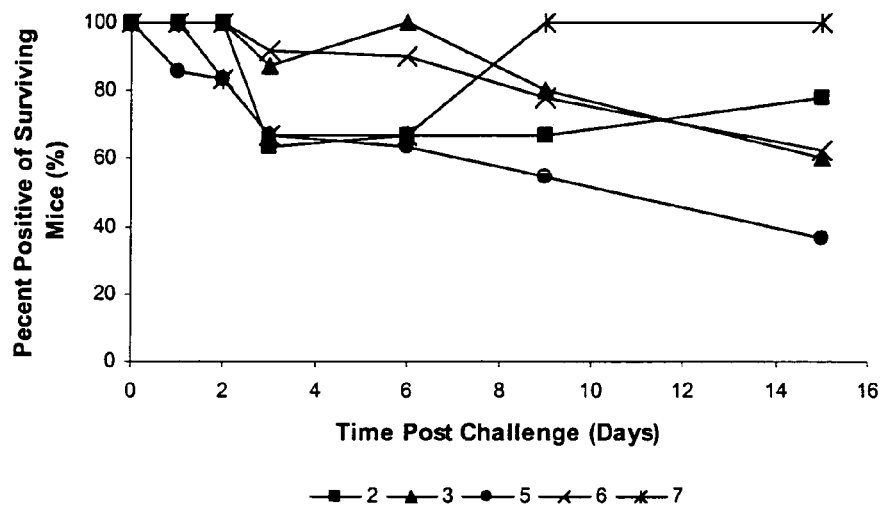
FIG. 24: Graph of the percentage of surviving swab positive mice in each group for Example 3. Groups 2 3, 5, 6 and 7 are shown.
Group 2 J14 amino terminal anchor/proteosome adjuvant (ratio A)—Quackenbush—Intranasal
Group 3 J14 amino terminal anchor/proteosome adjuvant (ratio B)—Quackenbush—Intranasal
Group 5 J14 carboxyl terminal anchor/proteosome adjuvant (ratio A)—Quackenbush—Intranasal
Group 6 J14 carboxyl terminal anchor/proteosome adjuvant (ratio B)—Quackenbush—Intranasal
Group 7 Proteosome adjuvant only—Quackenbush—Intranasal

The percentage of mice surviving in each group from the total of mice that were originally challenged in that group were ascertained. By day 15 all peptide/proteosome adjuvant immnunised groups had reduced number of mice either dead or swab positive when compared to the proteosome adjuvant only immunised group (FIG. 22).

Example 4d

Percent Positive of Surviving Mice

This data indicates the percentage of mice that produced a GAS positive throat swab out of the surviving mice in each group at the designated day on which the swab was taken.

Of the surviving mice the J14 immunised mice had a reduction in the number of mice that returned positive throat swabs. From the data obtained from examples 2 and 3, group 5 appears to be the best candidate of the formulations tested in the murine model. FIGS. 25 to 28 compare this group from example 3 to the corresponding control groups 7 (proteosome adjuvant only) and 8 (PBS).

Figure 27:
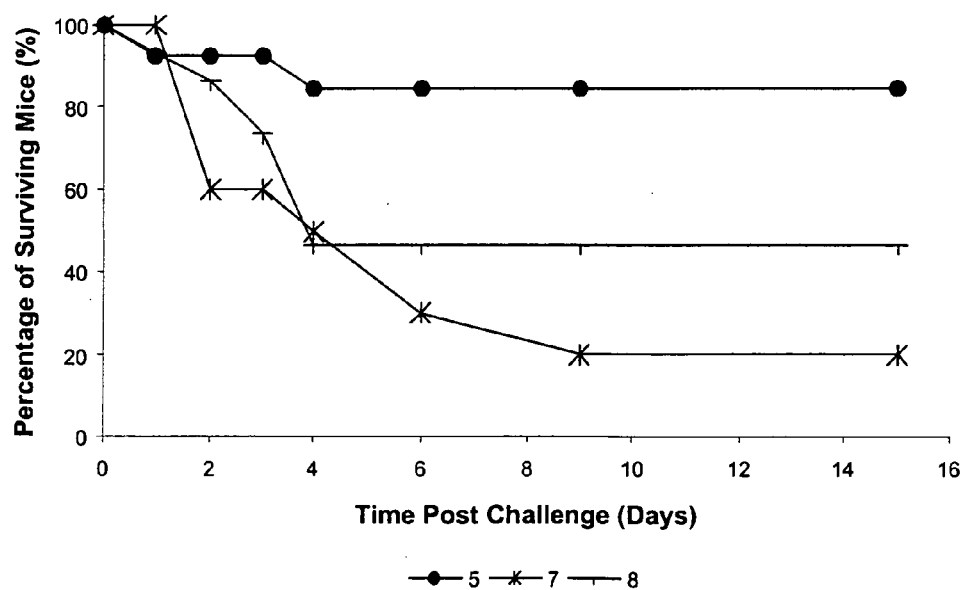
FIG. 27: Graph of the percentage of the surviving mice in each group post-intranasal challenge with GAS. Groups 5, 7 and 8 are shown for Example 3.
Group 5 J14 carboxyl terminal anchor/proteosome adjuvant (ratio A)—Quackenbush—Intranasal
Group 7 Proteosome adjuvant only—Quackenbush—Intranasal
Group 8 PBS—Quackenbush—Intranasal
Figure 28:
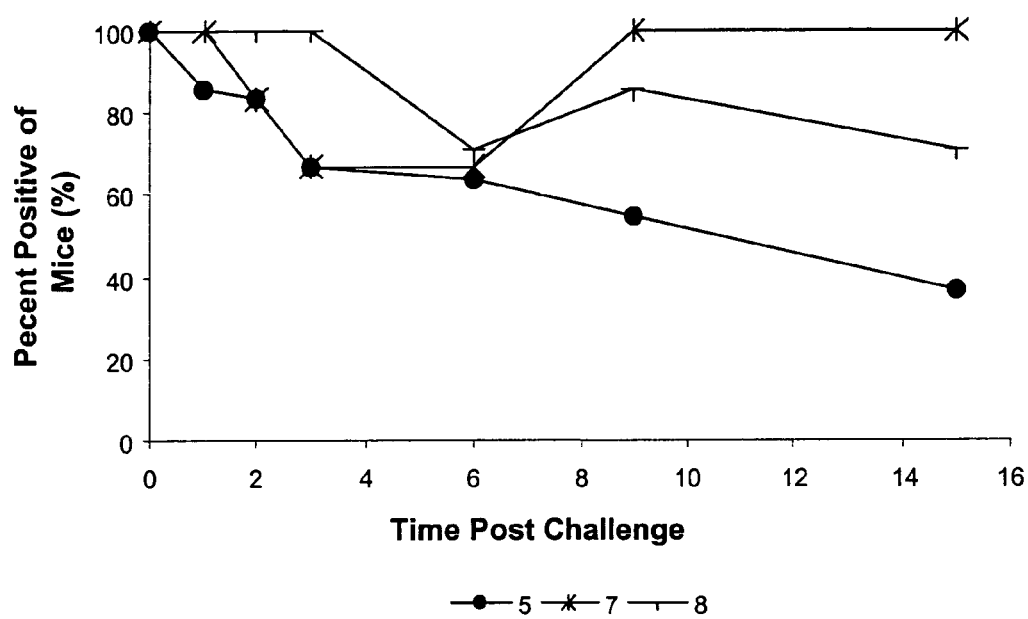
FIG. 28: Graph of the percentage of swab positive mice of the surviving mice in each group at the time of swabbing. Groups 5, 7 and 8 are shown for Example 3.
Group 5 J14 carboxyl terminal anchor/proteosome adjuvant (ratio A)—Quackenbush—Intranasal
Group 7 Proteosome adjuvant only—Quackenbush—Intranasal
Group 8 PBS—Quackenbush—Intranasal

By day 9 post challenge the J14 immunised mice (group 5) had a significant reduction in the number of animals that returned a positive swab or were dead when compared to the proteosome adjuvant only (group 7) and PBS (group 8) control groups. A comparison of group 5 and the control groups 7 (proteosome adjuvant only) and 8 (PBS) as shown in FIG. 27, found that the J14 immunised mice (group 5) had significantly more mice surviving challenge at day 6 compared to both groups 7 and 8. Group 5 also appeared to clear the GAS colonisation in the surviving mice—quicker then that of the control groups in which the majority of the mice died (100% positive in group 7 and 92.9% positive in group 8) (FIG. 28).

Discussion and Conclusions

The constructs delivered intranasally induced a strong IgG and IgA antibody response in the serum and saliva, respectively. In addition it was shown that the serum IgG antibodies were able to opsonise the GAS reference strain (M1) in vitro.

The J14 proteosome adjuvant formulations were able to delay death and reduce the initial bio-burden of the GAS challenge compared to the control groups. Group 5 was the best performer of the peptide proteosome adjuvant groups and was able to reduce the initial average C.F.U. of GAS colonisation by approximately 40% with in the first 24 hours. This group was also able to reduce the number of swab positive or dead mice in the group, had significant numbers of mice survive challenge and of those that survived, less returned positive swabs.

Tables 6 to 11 show the days on which there were significant differences in mice survival, percent positive (or dead) and percent positive of surviving mice between the peptide-proteosome adjuvant immunised groups (2, 3, 5 and 6) and the proteosome adjuvant only and PBS control groups (groups 7 and 8, respectively).

TABLE 6

Significance Summary of Mice Survival Post-Challenge Data (Example 3).
P values shown, dark grey P < 0.05 and light grey P < 0.1. Groups 2, 3, 5, 6 v 7.
(Number of Surviving Mice/Number of Mice Challenged).

| Day | Group 2 proteosome adjuvant: nJ14(1:2.2) | Group 3 proteosome adjuvant: nJ14(1:4.1) | Group 5 proteosome adjuvant: cJ14(1:1.6) | Group 6 proteosome adjuvant: cJ14(1:4.6) | Group 7 proteosome adjuvant only |
|---|---|---|---|---|---|
| 1 | 1.00 (11/11) | 0.329 (12/14) | 0.583 (13/14) | 1.000 (15/15) | -(10/10) |
| 2 | 0.035 (11/11) | 0.295 (11/14) | 0.075 (13/14) | 0.147 (13/15) | -(6/10) |
| 3 | 0.126 (10/11) | 0.611 (8/14) | 0.075 (13/14) | 0.261 (12/15) | -(6/10) |
| 4 | 0.055 (10/11) | 0.660 (7/14) | 0.075 (12/14) | 0.337 (10/15) | -(5/10) |
| 5 | 0.055 (10/11) | 0.660 (7/14) | 0.075 (12/14) | 0.337 (10/15) | -(5/10) |
| 6 | 0.024 (9/11) | 0.418 (6/14) | 8.8 × 10⁻⁴ (12/14) | 0.082 (10/15) | -(3/10) |
| 7 | 0.024 (9/11) | 0.418 (6/14) | 8.8 × 10⁻⁴ (12/14) | 0.082 (10/15) | -(3/10) |
| 8 | 0.024 (9/11) | 0.418 (6/14) | 8.8 × 10⁻⁴ (12/14) | 0.082 (10/15) | -(3/10) |
| 9 | 7.3 × 10⁻³ (9/11) | 0.357 (5/14) | 2.1 × 10⁻⁴ (12/14) | 0.057 (9/15) | -(2/10) |
| 10 | 7.3 × 10⁻³ (9/11) | 0.357 (5/14) | 2.1 × 10⁻⁴ (12/14) | 0.057 (9/15) | -(2/10) |
| 11 | 7.3 × 10⁻³ (9/11) | 0.357 (5/14) | 2.1 × 10⁻⁴ (12/14) | 0.057 (9/15) | -(2/10) |
| 12 | 7.3 × 10⁻³ (9/11) | 0.357 (5/14) | 2.1 × 10⁻⁴ (12/14) | 0.057 (9/15) | -(2/10) |
| 13 | 7.3 × 10⁻³ (9/11) | 0.357 (5/14) | 2.1 × 10⁻⁴ (12/14) | 0.057 (9/15) | -(2/10) |
| 14 | 7.3 × 10⁻³ (9/11) | 0.357 (5/14) | 2.1 × 10⁻⁴ (12/14) | 0.057 (9/15) | -(2/10) |
| 15 | 7.3 × 10⁻³ (9/11) | 0.357 (5/14) | 2.1 × 10⁻⁴ (12/14) | 0.105 (8/15) | -(2/10) |

TABLE 7

Significance Summary of Mice Culture Positive or Dead Post-Challenge
Data (Example 3). P values shown, dark grey P < 0.05 and light grey P < 0.1. Groups
2, 3, 5, 6 v 7

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 7 proteosome adjuvant only |
|---|---|---|---|---|---|
| 1 | 1.000 | 1.000 | 0.329 | 1.000 | — |
| 2 | 0.454 | 0.417 | 0.602 | 0.399 | — |
| 3 | 0.417 | 0.371 | 0.463 | 0.346 | — |
| 6 | 0.331 | 0.417 | 0.250 | 0.650 | — |
| 9 | 0.124 | 0.583 | 0.048 | 0.350 | — |
| 15 | 0.262 | 0.329 | 0.007 | 0.198 | — |

TABLE 8

Significance Summary of Surviving Mice Culture Positive Post-Challenge
Data (Example 3). P values shown, dark grey P < 0.05 and light
grey P < 0.1. Groups 2,3,5,6 v 7 (Number of Swab Positive
Mice/Number of Surviving Mice)

| Day | Group 2 proteosome adjuvant: nJ14(1:2.2) | Group 3 proteosome adjuvant: nJ14(1:4.1) | Group 5 proteosome adjuvant: cJ14(1:1.6) | Group 6 proteosome adjuvant: cJ14(1:4.6) | Group 7 proteosome adjuvant only |
|---|---|---|---|---|---|
| 1 | 1.000 (12/12) | 1.000 (14/14) | 0.329 (12/14) | 1.000 (15/15) | -(10/10) |
| 2 | 0.333 (12/12) | 0.353 (11/11) | 0.730 (10/12) | 0.316 (13/13) | -(5/6) |
| 3 | 0.662 (7/11) | 0.385 (7/8) | 0.694 (8/12) | 0.245 (11/12) | -(4/6) |
| 6 | 0.745 (6/9) | 0.333 (6/6) | 0.725 (7/11) | 0.423 (9/10) | -(2/3) |
| 9 | 0.509 (6/9) | 0.714 (4/5) | 0.358 (6/11) | 0.654 (7/9) | -(2/2) |
| 15 | 0.654 (7/9) | 0.476 (3/5) | 0.192 (4/11) | 0.466 (5/8) | -(2/2) |

TABLE 9

Significance Summary of Mice Survival Post-Challenge Data (Example 3).
P values shown, dark grey P < 0.05 and light grey P < 0.1. Groups 2, 3, 5, 6 v 8. (Number of Surviving Mice/Number of Mice Challenged).

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 8 PBS |
|---|---|---|---|---|---|
| 1  | 0.577 (11/11) | 0.473 (12/14) | 0.741 (13/14) | 0.499 (15/15) | -(14/15) |
| 2  | 0.303 (11/11) | 0.500 (11/14) | 0.500 (13/14) | 0.674 (13/15) | -(13/15) |
| 3  | 0.274 (10/11) | 0.299 (8/14)  | 0.186 (12/14) | 0.500 (12/15) | -(11/15) |
| 4  | 0.024 (10/11) | 0.576 (7/14)  | 0.032 (12/14) | 0.231 (10/15) | -(7/15) |
| 5  | 0.024 (10/11) | 0.576 (7/14)  | 0.032 (12/14) | 0.231 (10/15) | -(7/15) |
| 6  | 0.109 (9/11)  | 0.566 (6/14)  | 0.032 (12/14) | 0.231 (10/15) | -(7/15) |
| 7  | 0.109 (9/11)  | 0.566 (6/14)  | 0.032 (12/14) | 0.231 (10/15) | -(7/15) |
| 8  | 0.109 (9/11)  | 0.566 (6/14)  | 0.032 (12/14) | 0.231 (10/15) | -(7/15) |
| 9  | 0.109 (9/11)  | 0.413 (5/14)  | 0.032 (12/14) | 0.357 (9/15)  | -(7/15) |
| 10 | 0.109 (9/11)  | 0.413 (5/14)  | 0.032 (12/14) | 0.357 (9/15)  | -(7/15) |
| 11 | 0.109 (9/11)  | 0.413 (5/14)  | 0.032 (12/14) | 0.357 (9/15)  | -(7/15) |
| 12 | 0.109 (9/11)  | 0.413 (5/14)  | 0.032 (12/14) | 0.357 (9/15)  | -(7/15) |
| 13 | 0.109 (9/11)  | 0.413 (5/14)  | 0.032 (12/14) | 0.357 (9/15)  | -(7/15) |
| 14 | 0.109 (9/11)  | 0.413 (5/14)  | 0.032 (12/14) | 0.357 (9/15)  | -(7/15) |
| 15 | 0.109 (9/11)  | 0.413 (5/14)  | 0.032 (12/14) | 0.500 (8/15)  | -(7/15) |

TABLE 10

Significance Summary of Mice Culture Positive or Dead Post-Challenge Data (Example 3). P values shown, dark grey P < 0.05 and light grey P < 0.1. Groups 2, 3, 5, 6 v 8.

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 8 PBS |
|---|---|---|---|---|---|
| 1  | 1.000 | 1.000 | 0.224 | 1.000 | — |
| 2  | 1.000 | 1.000 | 0.206 | 1.000 | — |
| 3  | 0.028 | 0.483 | 0.035 | 0.499 | — |
| 6  | 0.346 | 0.259 | 0.255 | 0.499 | — |
| 9  | 0.188 | 0.741 | 0.056 | 0.500 | — |
| 15 | 0.574 | 0.674 | 0.029 | 0.500 | — |

TABLE 11

Significance Summary of Surviving Mice Culture Positive Post-Challenge Data (Example 3). P values shown; dark grey P < 0.05 and light grey P < 0.1 values shaded. Groups 2,3,5,6 v 8. (Number of Swab Positive Mice/Number of Surviving Mice).

| Day | Group 2 proteosome adjuvant: nJ14 (1:2.2) | Group 3 proteosome adjuvant: nJ14 (1:4.1) | Group 5 proteosome adjuvant: cJ14 (1:1.6) | Group 6 proteosome adjuvant: cJ14 (1:4.6) | Group 8 PBS |
|---|---|---|---|---|---|
| 1  | 1.000 (12/12) | 1.000 (14/14) | 0.224 (12/14) | 1.000 (15/15) | (15/15) |
| 2  | 1.000 (12/12) | 1.000 (11/11) | 0.203 (10/12) | 1.000 (13/13) | (14/14) |
| 3  | 0.045 (7/11)  | 0.421 (7/8)   | 0.056 (8/12)  | 0.522 (11/12) | (11/11) |
| 6  | 0.635 (6/9)   | 0.269 (6/6)   | 0.572 (7/11)  | 0.360 (9/10)  | (5/7) |
| 9  | 0.392 (6/9)   | 0.688 (4/5)   | 0.199 (6/11)  | 0.600 (7/9)   | (6/7) |
| 15 | 0.607 (7/9)   | 0.576 (3/5)   | 0.167 (4/11)  | 0.573 (5/8)   | (5/7) |

TABLE 12

Preliminary analysis of vaccines composition: initial and final [Proteosome adjuvant:Peptide] ratios

| Vaccine | Theoretical initial ratio [Proteosome adjuvant: Peptide][1] | Actual initial ratio [Proteosome: adjuvant Peptide][2] | Determined Proteosome adjuvant final[3] (mg) | Calculated Peptide final[4] (mg) | Final ratio [Proteosome adjuvant Peptide] | Final Volume (ml) | | Calculated Peptide final concentration[5] (mg/ml) | Estimated Peptide final concentration (mg/ml) |
|---|---|---|---|---|---|---|---|---|---|
| N-terminal | | | | | | | | | |
| A | 1:2 | 1:1.6 | 19.5 | 42.1 | 1:2.2 | As formulated | 15.0 | 2.8 | 2.8 |
|   |     |       |      |      |       | As diluted for delivery | 21.0 | 2.0 | 2.0 |
| B | 1:7 | 1:5.7 | 7.4  | 30.3 | 1:4.1 | As formulated | 11.0 | 2.8 | 2.5 |
|   |     |       |      |      |       | As diluted for delivery | 13.8 | 2.2 | 2.0 |
| C-terminal | | | | | | | | | |
| A | 1:2 | 1:1.3 | 18.4 | 30.2 | 1:1.6 | As formulated | 15.0 | 2.0 | 2.0 |
|   |     |       |      |      |       | As diluted for delivery | 15.0 | 2.0 | 2.0 |
| B | 1:7 | 1:4.5 | 5.4  | 25.1 | 1:4.6 | As formulated | 11.0 | 2.3 | 2.1 |
|   |     |       |      |      |       | As diluted for delivery | 11.6 | 2.2 | 2.0 |

[1]Using peptide determined by dry weight as reported by vendor, without correction for peptide content
[2]Using peptide concentration as determined by AAA
[3]From Coomassie blue-strained SDS-PAGE densitometry
[4]Calculated Peptide = Total protein (Lowry) − Proteosome adjuvant (SDS-PAGE densitometry)
[5]According to calculated peptide final and final

TABLE 13

Results from parenteral immunisation with the selected MtsA (A) and APP (B) antigens and subsequent parenteral GAS challenge.

| Antigen | Percentage of surviving mice | Opsonic Activity % |
|---|---|---|
| A | | |
| PBS (-ve) Expt #1 | 50 | 0 |
| MtsA (EIN) Expt #1 | 75 | 60 |
| PBS (−ve) Expt #2 | 40 | 0 |
| MtsA (EIN) Expt #2 | 90 | 84 |
| B | | |
| PBS (-ve) | 40 | 0 |
| APP chimeric | 73.3 | 45 |

The J14 peptide derived from the conserved region of the outer membrane M protein of Streptococcus pyogenes was evaluated together with the proteosome adjuvant. After intranasal immunisation with the J14 carboxyl terminal anchor proteosome complex and subsequent intranasal challenge, 85-90% protection was observed. The in vitro analysis showed that the formulation induced opsonic antibodies in sera and secretory antibodies in saliva.

This patent application describes the evaluation of the J14 peptide/proteosome adjuvant complex as a potential intranasal vaccine for GAS. The J14 peptide, constituting a highly conserved region of the M protein, has been used as a representative antigen to illustrate the feasibility and efficacy of the vaccine.

In addition to this peptide, MtsA and APP peptides have also been demonstrated to effectively induce high opsonic activity and protection in mice intraperitoneal challenge models (table 13). A study of the Thai GAS endemic population shows that both of these antigens and their peptide derivatives are widely recognised (85%) by antibodies. Based on these data, two peptide candidates (EIN 19 and APP chimeric KQL30) have been selected for further pre-clinical studies in the proteosome adjuvant formulation.

Bessen and Fischetti (1990) reported the influence of intranasal immunisation with synthetic peptides corresponding to conserved epitopes of the M protein on mucosal colonisation by GAS. Mice were immunised intranasally with conserved region peptide—CTB conjugates or CTB only. Mice were then challenged with GAS and monitored for 15 days post challenge.

After fifteen days post challenge, 28.8% of CTB immunised mice and peptide—CTB immunised mice were dead, compared to 80% and 15.4% of proteosome adjuvant only and peptide proteosome adjuvant immunised mice (group 5), respectively, demonstrated in this patent application. By day 15, 65.4% of CTB immunised mice and 46.2% of peptide—CTB immunised mice were either swab positive or dead. Comparing this to our current study, which found that 15 days after challenge 100% of proteosome adjuvant only and 42.8% of peptide proteosome adjuvant immunised mice (group 5) were swab positive or dead.

Of the surviving mice at day 15, Bessen and Fischetti reported 51% and 24% positive for GAS in the CTB immunised mice and peptide—CTB immunised mice, respectively. In comparison 100% and 36.4% of the proteosome adjuvant only and peptide proteosome adjuvant immunised mice (group 5) respectively were positive for GAS in the studies described within this application.

In a separate study, Guzman et al, (1999) reported a protective immune response against Streptococcus pyogenes in mice following intranasal vaccination with the fibronectin-binding protein, SfbI. Outbred Swiss mice were intranasally immunised with SfbI coupled to CTB and then challenged intranasally. Five days post challenge 100% of the CTB mice and 20% of the SfbI mice were dead.

Using heat-killed bacteria, Bronze et. al., (1992), reported that a locally administered group A streptococcal vaccine in mice could evoke protective immunity. Outbred Swiss mice were intranasally immunised with heat-killed GAS and then challenge intranasally. Fourteen days post challenge 83.3% of PBS and 0% of heat-killed GAS immunised mice were dead.

Ji et. al. (1997) immunised mice intranasally with affinity purified recombinant C5a peptidase and reported 10.5% of these mice were culture positive on day 5 post challenge, in contrast to 37% of PBS immunised mice. In comparison, the data presented within this application shows that by day 6 post challenge 64.3% of peptide-proteosome adjuvant immunised mice (group 5) were swab positive or dead and 90% of proteosome adjuvant only mice were swab positive or dead.

The J14-proteosome adjuvant immunised mice described herein appear to have increased levels of protection against GAS when compared to the Bessen and Fischetti study. The percentage of survival of these groups was also comparable to that achieved with the Sfbl protein, the whole heat killed bacteria and C5a peptidase immunised mice.

REFERENCES

1. Cartwright K. 1997 "Group A streptococcus infections in humans." J Appl. Microbiol. Symp. Suppl. 83: 52S-61S.
2. Robinson J H & Kehoe M A 1992 "Group streptococcal M proteins: virulence factors and protective antigens." Immunol Today 13: 362-367.
3. Kehoe M A, Kapur V, Whatmore A M & Musser J M. 1996 "Horizontal gene transfer among group A streptococci: implications for pathogenesis and epidemiology." Trends Microbiol. 4: 436-443.
4. Johnsson E et al 1998 "Role of hypervariable region in streptococcal M proteins: Binding of human complement inhibitor." J Immunol 161(9): 4894-4901.
5. Pruksakom S. et al 1994 "Towards a vaccine for rheumatic fever: identification of a conserved target epitope on M protein of group A streptococci." Lancet 344, 639-642.
6. Pruksakom et al 1994 "Identification of T-cell autoepitopes that cross-react with the carboxterminal segment of the M protein of Group A streptococci. Int. Immunol., 6, 1235-1244.
7. Relf W A et al. 1996 "Mapping a conserved conformational from the M protein of group A streptococci." Peptide Res 9:12-20.
8. Hayman W A et al. 1997 "Mapping the minimal T and B cell epitope within the peptide vaccine candidate from the conserved region of the M protein of group A streptococci." Int. Immunol 9 1723-1733.
9. Brandt E et al. 2000 "New multi-determinant strategy for a group A streptococcal vaccine designed for the Australian Aboriginal population." Nature Medicine 6(4): 455-459.
10. Janulczyk R et al. 1999 "Identification and characterisation of a Streptoccoccus pyogenes ABC transporter with multiple specificity for metal cations." Mol Microbiol 34: 596-606.
11. Bessen D E & Fischetti V A 1990 "Synthetic peptide vaccine against mucosal colonization by group A streptococci.I. protection against a heterologous M serotype with shared C repeat region epitopes" J Immunol 145(4): 1251-6.
12. Ji Y et al 1997 "Intranasal immunisation with C5a peptidase prevents nasopharyngeal colonization of mice by group A streptococcus " Infect Immun 65(6): 2080-7.
13. Bronze M S et al 1992 "Epitopes of group A streptococcal M protein that evoke cross-protective local immune responses". J Immunol 148(3): 888-93.
14. Guzman C A et al 1999 "Protective immune response against Streptococcus pyogenes in mice after intranasal vaccination with fibronectin-binding protein SfbI." J Infect Dis 179(4): 901-6.
15. Lowell G H et al 1988 "Proteosome and hydrophobic foot vaccines provide enhanced immunogenicity of malaria, trypanosome and streptococcal peptides without added adjuvants" In: Technical Advances in Vaccine Development" L. Lasky Ed, Alan R. Liss, N pp 423-432.

The invention claimed is:

1. A vaccine composition comprising a proteosome adjuvant and a group A Streptococcal antigen that comprises an antigenic peptide between 15 and 30 amino acids in length from the conserved C-terminal region of an *S. pyogenes* M protein, wherein the antigenic peptide comprises the amino acid sequence ASREAKKQVEKALE (SEQ ID NO:1), and wherein the antigen is attached to a hydrophobic moiety.

2. The vaccine composition according to claim 1 wherein the antigen comprises the antigenic peptide flanked by amino acid sequences to maintain helical folding of the antigen.

3. The vaccine composition according to claim 2 wherein the antigen comprises the sequence KQAEDKVKAS-REAKKQVEKALEQLEDKVK(SEQ ID NO:2).

4. The vaccine composition according to claim 1 wherein the hydrophobic moiety is attached at the N-terminal end or C-terminal end of the antigen for complexing the antigen with the proteosome adjuvant.

5. The vaccine composition according to claim 1 wherein the composition is formulated for mucosal administration.

6. The vaccine composition according to claim 5 wherein mucosal administration is intranasal.

7. The vaccine composition according to claim 1 wherein administration of the composition to an individual induces a mucosal immune response.

8. The vaccine composition according to claim 1, wherein administration of the vaccine composition induces a serum immune response.

9. The vaccine composition according to claim 5 wherein the vaccine composition is capable of treating or preventing a group A Streptococcal infection via reducing or preventing streptococcal group A bacterial colonisation of the throat.

10. A method of treatment or prophylaxis of group A Streptococcal infection in an individual comprising administering the vaccine composition according to claim 1 to the individual.

11. The method according to claim 10 wherein said vaccine composition is administered intranasally to said individual.

12. The method according to claim 11 wherein the treatment or prophylaxis of the group A Streptococcal infection is produced via prevention or reduction of bacterial colonisation of the throat.

13. The vaccine composition according to claim 1 wherein the antigen further comprises a spacer peptide comprising at least two glycine residues, and wherein the spacer peptide links the antigenic peptide and the hydrophobic moiety.

* * * * *

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: antigenic peptide sequence derivative of S.
      pyogenes

<400> SEQUENCE: 1

Ala Ser Arg Glu Ala Lys Lys Gln Val Glu Lys Ala Leu Glu
1               5                   10

<210> SEQ ID NO 2
<211> LENGTH: 29
<212> TYPE: PRT
<213> ORGANISM: Artificial Sequence
<220> FEATURE:
<223> OTHER INFORMATION: antigenic peptide derivative of S. pyogenes
      with flanking sequences

<400> SEQUENCE: 2

Lys Gln Ala Glu Asp Lys Val Lys Ala Ser Arg Glu Ala Lys Lys Gln
1               5                   10                  15
```

```
Val Glu Lys Ala Leu Glu Gln Leu Glu Asp Lys Val Lys
            20                  25

<210> SEQ ID NO 3
<211> LENGTH: 19
<212> TYPE: PRT
<213> ORGANISM: Artificial Sequence
<220> FEATURE:
<223> OTHER INFORMATION: antigenic peptide sequence  EIN19

<400> SEQUENCE: 3

Glu Ile Asn Thr Glu Glu Glu Gly Thr Pro Asp Gln Ile Ser Ser Leu
1               5                   10                  15

Ile Glu Lys

<210> SEQ ID NO 4
<211> LENGTH: 30
<212> TYPE: PRT
<213> ORGANISM: Artificial Sequence
<220> FEATURE:
<223> OTHER INFORMATION: antigenic peptide sequence KQL30

<400> SEQUENCE: 4

Lys Gln Leu Glu Asp Arg Val Gln Gln Leu Glu Thr Glu Lys Gln Ile
1               5                   10                  15

Ser Glu Ala Ser Arg Lys Ser Ala Glu Asp Lys Val Lys Gln
            20                  25                  30

<210> SEQ ID NO 5
<211> LENGTH: 20
<212> TYPE: PRT
<213> ORGANISM: Artificial Sequence
<220> FEATURE:
<223> OTHER INFORMATION: antigenic peptide sequence p145

<400> SEQUENCE: 5

Leu Arg Arg Asp Leu Asp Ala Ser Arg Glu Ala Lys Lys Gln Val Glu
1               5                   10                  15

Lys Ala Leu Glu
            20

<210> SEQ ID NO 6
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 6

Gln Leu Glu Asp Lys Val Lys Gln Leu Arg Arg Asp Leu Asp Ala Ser
1               5                   10                  15

Arg Glu Ala Lys Glu Glu Leu Gln Asp Lys Val Lys
            20                  25

<210> SEQ ID NO 7
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 7

Leu Glu Asp Lys Val Lys Gln Ala Arg Arg Asp Leu Asp Ala Ser Arg
```

```
                  1               5                  10                  15
Glu Ala Lys Lys Glu Leu Gln Asp Lys Val Lys Gln
                 20                  25

<210> SEQ ID NO 8
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 8

Glu Asp Lys Val Lys Gln Ala Glu Arg Asp Leu Asp Ala Ser Arg Glu
1               5                  10                  15

Ala Lys Lys Gln Leu Gln Asp Lys Val Lys Gln Leu
                 20                  25

<210> SEQ ID NO 9
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 9

Asp Lys Val Lys Gln Ala Glu Asp Asp Leu Asp Ala Ser Arg Glu Ala
1               5                  10                  15

Lys Lys Gln Val Gln Asp Lys Val Lys Gln Leu Glu
                 20                  25

<210> SEQ ID NO 10
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 10

Lys Val Lys Gln Ala Glu Asp Lys Leu Asp Ala Ser Arg Glu Ala Lys
1               5                  10                  15

Lys Gln Val Glu Asp Lys Val Lys Gln Leu Glu Asp
                 20                  25

<210> SEQ ID NO 11
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 11

Val Lys Gln Ala Glu Asp Lys Val Asp Ala Ser Arg Glu Ala Lys Lys
1               5                  10                  15

Gln Val Glu Lys Lys Val Lys Gln Leu Glu Asp Lys
                 20                  25

<210> SEQ ID NO 12
<211> LENGTH: 28
<212> TYPE: PRT
<213> ORGANISM: Artificial Sequence
<220> FEATURE:
```

```
<223> OTHER INFORMATION: antigenic peptide sequence derivative of p145
      base

<400> SEQUENCE: 12

Lys Gln Ala Glu Asp Lys Val Lys Ala Ser Arg Glu Ala Lys Lys Gln
1               5                   10                  15

Val Glu Lys Ala Val Lys Gln Leu Glu Asp Lys Val
                20                  25

<210> SEQ ID NO 13
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 13

Gln Ala Glu Asp Lys Val Lys Gln Ser Arg Glu Ala Lys Lys Gln Val
1               5                   10                  15

Glu Lys Ala Leu Lys Gln Leu Glu Asp Lys Val Gln
                20                  25

<210> SEQ ID NO 14
<211> LENGTH: 28
<212> TYPE: PRT
<213> ORGANISM: Artificial Sequence
<220> FEATURE:
<223> OTHER INFORMATION: antigenic peptide sequence derivative of p145
      base

<400> SEQUENCE: 14

Ala Glu Asp Lys Val Lys Gln Leu Arg Glu Ala Lys Lys Gln Val Glu
1               5                   10                  15

Lys Ala Leu Glu Gln Leu Glu Asp Lys Val Gln Leu
                20                  25

<210> SEQ ID NO 15
<211> LENGTH: 29
<212> TYPE: PRT
<213> ORGANISM: Artificial Sequence
<220> FEATURE:
<223> OTHER INFORMATION: antigenic peptide sequence derivative of p145
      base

<400> SEQUENCE: 15

Lys Gln Ala Glu Asp Lys Val Lys Ala Ser Arg Glu Ala Lys Lys Gln
1               5                   10                  15

Val Glu Lys Ala Leu Glu Gln Leu Glu Asp Lys Val Lys
                20                  25
```